(12) United States Patent
Plos

(10) Patent No.: US 7,399,319 B2
(45) Date of Patent: Jul. 15, 2008

(54) DYEING COMPOSITION COMPRISING A DYE CHOSEN FROM STYRYL AND IMINE DYES AND METHODS FOR DYEING KERATIN FIBERS

(75) Inventor: Grégory Plos, Tokyo (JP)

(73) Assignee: L'Oreal S.A., Paris (FR)

( * ) Notice: Subject to any disclaimer, the term of this patent is extended or adjusted under 35 U.S.C. 154(b) by 179 days.

(21) Appl. No.: 11/491,109

(22) Filed: Jul. 24, 2006

(65) Prior Publication Data

US 2007/0174977 A1 Aug. 2, 2007

Related U.S. Application Data

(60) Provisional application No. 60/701,970, filed on Jul. 25, 2005.

(30) Foreign Application Priority Data

Jul. 22, 2005 (FR) .................... 05 52277

(51) Int. Cl.
*A61Q 5/10* (2006.01)
*C07D 263/04* (2006.01)

(52) U.S. Cl. .............. 8/405; 8/406; 8/414; 8/423; 8/426; 8/435; 8/565; 8/566; 8/567; 8/570; 8/571; 8/574; 8/606; 8/616; 548/217; 132/202; 132/208

(58) Field of Classification Search .......... 8/405, 8/406, 414, 423, 426, 435, 565, 566, 567, 8/570, 571, 606, 616; 132/202, 208; 548/217

See application file for complete search history.

(56) References Cited

U.S. PATENT DOCUMENTS

| 4,003,633 | A | 1/1977 | Yamashita |
| 4,139,274 | A | 2/1979 | Yamashita et al. |
| 4,147,862 | A | 4/1979 | Hayami et al. |
| 4,314,058 | A | 2/1982 | Hayami et al. |
| 4,340,624 | A | 7/1982 | Yamashita et al. |
| 4,380,629 | A * | 4/1983 | Yamashita et al. .......... 548/217 |
| 5,474,578 | A | 12/1995 | Chan et al. |

FOREIGN PATENT DOCUMENTS

| DE | 25 41 665 | 4/1976 |
| FR | 2 285 438 | 4/1976 |
| FR | 2 285 439 | 4/1976 |
| FR | 2 293 024 | 6/1976 |
| JP | 55-31057 | 3/1980 |
| JP | 55-113710 | 9/1980 |
| JP | 56-25106 | 3/1981 |
| JP | 56-81522 | 7/1981 |
| JP | 56-149489 | 11/1981 |
| JP | 56-150006 | 11/1981 |
| JP | 56-161489 | 12/1981 |
| JP | 57-14652 | 1/1982 |
| JP | 58-48031 | 3/1983 |
| JP | 59-52193 | 3/1984 |
| JP | 59-121319 | 7/1984 |
| JP | 60-57320 | 4/1985 |
| JP | 60-57322 | 4/1985 |
| JP | 60-57323 | 4/1985 |
| JP | 60-200233 | 10/1985 |
| JP | 61-121040 | 6/1986 |
| JP | 61-147235 | 7/1986 |
| JP | 63-280727 | 11/1988 |
| JP | 2-179618 | 7/1990 |
| JP | 8-222268 | 8/1996 |
| JP | 10-114151 | 5/1998 |
| JP | 11-34489 | 2/1999 |
| JP | 11-34497 | 2/1999 |
| JP | 2000-292817 | 10/2000 |
| JP | 2001-81342 | 3/2001 |
| JP | 2001-109021 | 4/2001 |
| JP | 2001-246862 | 9/2001 |
| JP | 2003-315839 | 11/2003 |

OTHER PUBLICATIONS

STIC Search Report dated Mar. 12, 2008.*
French Search Report for FR 0552277, dated Apr. 20, 2006.
English language abstract of JP 55-31057, Mar. 5, 1980.
English language abstract of JP 55-113710, Sep. 2, 1980.
English language abstract of JP-56-81522, Jul. 3, 1981.
English language abstract of JP 56-25106, Mar. 10, 1981.
English language abstract of JP 57-14652, Jan. 25, 1982.
English language abstract of JP 56-150006, Nov. 20, 1981.
English language abstract of JP 56-161489, Dec. 11, 1981.
English language abstract of JP 58-48031, Mar. 19, 1983.
English language abstract of JP 59-52193, Mar. 26, 1984.
English language abstract of JP 59-121319, Jul. 13, 1984.
English language abstract of JP 60-57320, Apr. 3, 1985.
English language abstract of JP 60-57322, Apr. 3, 1985.
English language abstract of JP 60-57323, Apr. 3, 1985.

(Continued)

*Primary Examiner*—Eisa B Elhilo
(74) *Attorney, Agent, or Firm*—Finnegan, Henderson, Farabow, Garrett & Dunner L.L.P.

(57) ABSTRACT

Disclosed herein is a method for dyeing keratin fibers, for example, human keratin fibers such as the hair, comprising applying to the keratin fibers a dye composition comprising at least one compound chosen from styryl and imine compounds comprising a heterocycle that can undergo opening and/or dyes corresponding to these compounds whose heterocycles are open. The compositions and methods of the present disclosure may produce a coloration of keratin fibers that is chromatic and fast with respect to external factors such as shampooing, does not stain, and/or allows simultaneous dyeing and bleaching of keratin fibers.

35 Claims, No Drawings

OTHER PUBLICATIONS

English language abstract of JP 60-200233, Oct. 9, 1985.
English language abstract of JP 61-121040, Jun. 9, 1986.
English language abstract of JP 61-147235, Jul. 4, 1986.
English language abstract of Jp 63-280727, Nov. 17, 1988.
English language abstract of JP 2-179618, Jul. 12, 1990.
English language abstract of JP 8-222268, Aug. 30, 1996.
English language abstract of JP 10-114151, May 6, 1998.
English language abstract of JP 11-34489, Feb. 9, 1999.
English language abstract of JP 11-34497, Feb. 9, 1999.
English language abstract of JP 2000-292817, Oct. 20, 2000.
English language abstract of JP 2001-81342, Mar. 27, 2001.
English language abstract of JP 2001-109021, Apr. 20, 2001.
English language abstract of JP 2001-246862, Sep. 11, 2001.
English language abstract of JP 2003-315839, Nov. 6, 2003.

* cited by examiner

DYEING COMPOSITION COMPRISING A DYE CHOSEN FROM STYRYL AND IMINE DYES AND METHODS FOR DYEING KERATIN FIBERS

CROSS-REFERENCE TO RELATED APPLICATIONS

This application claims benefit of U.S. Provisional Application No. 60/701,970, filed Jul. 25, 2005, the contents of which are incorporated herein by reference. This application also claims benefit of priority under 35 U.S.C. § 119 to French Patent Application No. FR 05 52277, filed Jul. 22, 2005, the contents of which are also incorporated herein by reference.

FIELD OF THE INVENTION

Disclosed herein is a method for dyeing keratin fibers, for example, human keratin fibers such as the hair, comprising applying to the keratin fibers a composition comprising at least one dye chosen from styryl and imine dyes.

BACKGROUND OF THE INVENTION

It is known practice to dye keratin fibers, for example, human keratin fibers such as the hair, with dye compositions comprising oxidation dye precursors, which are generally known as oxidation bases, such as ortho- or para-phenylenediamines, ortho- or para-aminophenols, and heterocyclic compounds such as diaminopyrazole derivatives. These oxidation bases are colorless or weakly colored compounds, which, when combined with oxidizing products, may give rise to colored compounds via a process of oxidative condensation.

It is also known that the shades obtained with these oxidation bases can be varied by combining them with couplers or coloration modifiers, the latter being chosen, for example, from aromatic meta-diamines, meta-aminophenols, meta-diphenols, and heterocyclic compounds such as indole compounds.

The variety of molecules used as oxidation bases and couplers allows a wide range of colors to be obtained.

The "permanent" coloration obtained by means of these oxidation dyes ideally satisfies at least one of a number of various characteristics. For example, the dye ideally has no toxicological drawbacks, allows shades to be obtained in the desired intensity, shows good fastness with respect to external agents such as light, bad weather, washing, permanent waving, perspiration, and/or rubbing, allows grey hair to be covered, and is as unselective as possible, i.e., produces the smallest possible color differences along the same keratin fiber, which is generally differently sensitized (i.e., damaged) between its end and its root.

It is also known practice to dye keratin fibers, for example, human keratin fibers such as the hair, with dye compositions comprising direct dyes. These dyes are colored and coloring molecules with an affinity for keratin fibers. They may be applied to the keratin fibers for a time necessary to obtain a desired coloration, and then may be rinsed out.

The standard direct dyes used include, for example, nitrobenzene dyes, anthraquinone dyes, nitropyridine dyes, azo dyes, cationic azo dyes, xanthene dyes, acridine dyes, azine dyes, triarylmethane dyes, and natural dyes.

The use of direct dyes is common since they have certain advantages over oxidation dye precursors, for example, reduction of the potential risks of allergy, absence of sensitization of the hair due to the oxidative process, and/or shorter leave-on times. In addition, the colorations obtained with direct dyes may be chromatic.

However, the colorations obtained with direct dyes may be temporary or semi-permanent, since the nature of the interactions that bind the direct dyes to the keratin fiber, and their desorption from the surface and/or the core of the fiber, are responsible for their low dyeing power and their poor fastness with respect to washing, bad weather, and/or perspiration. These direct dyes may also be light-sensitive due to the poor resistance of the chromophore to photochemical attack, which may lead over time to fading of the coloration of the hair.

Moreover, direct dye compositions are colored and, in oxidation dyeing, the coloration develops both in the composition and on the hair. Consequently, direct dyeing and oxidation dyeing have the drawback of making the application soiling.

Compounds of styryl and imine type existing in a colored form and in a colorless form and their use in the field of cosmetics, for example, in the field of skincare and nail varnishes, are described, for example, in Japanese Patent Nos. 56-150 006, 56-081 522, 56-025 106, 55-113 710, and 55-031 057.

DETAILED DESCRIPTION OF THE INVENTION

Disclosed herein, therefore, are novel compositions for dyeing keratin fibers that do not have at least one of the drawbacks of the prior art. For example, the dyes of the present disclosure may rapidly produce colorations which are chromatic and fast with respect to various external factors, such as shampooing, and which do not stain.

Also disclosed herein is a method for dyeing keratin fibers comprising applying to the keratin fibers a dye composition comprising, in a suitable dyeing medium, at least one compound chosen from compounds of formulas (I) and (II), and the addition salts thereof:

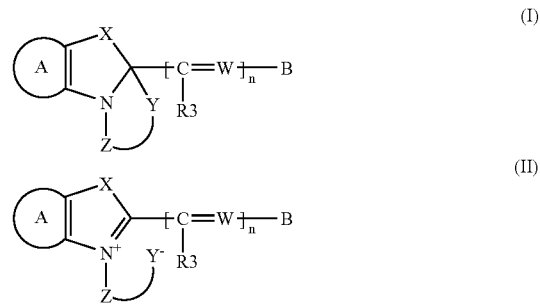

wherein:
A is chosen from substituted or unsubstituted, 5- to 16-membered, fused or non-fused aromatic or heteroaromatic nuclei;
X is chosen from oxygen, sulfur, and $CR_1R_2$ groups;
$R_1$ and $R_2$, which may be identical or different, are chosen from hydrogen, $C_1$-$C_6$ alkyl radicals, $C_1$-$C_6$ hydroxyalkyl radicals, $C_1$-$C_6$ alkoxyalkyl radicals, and alkylene chains optionally comprising at least one atom chosen from oxygen and sulfur atoms; and $R_1$ and $R_2$ may together form an aromatic or non-aromatic 5- or 6-membered ring optionally comprising at least one heteroatom chosen, for example, from nitrogen, oxygen, and sulfur;

$R_3$ is chosen from hydrogen, halogen atoms, $C_1$-$C_6$ alkyl radicals, cyano radicals, aromatic groups, phenoxy groups, and nitro radicals;

W is chosen from $CR_4$ groups and nitrogen;

$R_4$ is chosen from hydrogen, halogen atoms, $C_1$-$C_6$ alkyl radicals, cyano radicals, aromatic groups, phenoxy radicals, and nitro radicals.

Y is chosen from oxygen, sulfur, and $NR_5$ groups;

$R_5$ is chosen from hydrogen and $C_1$-$C_6$ alkyl radicals;

Z is chosen from —$C_pH_{2p}$— groups, wherein p is an integer ranging from 2 to 4, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals; and —$C_qH_{2q}CO$— groups, wherein q is an integer ranging from 1 to 3, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals;

n is an integer ranging from 1 to 4; and

B is chosen from substituted or unsubstituted, 5- to 16-membered, fused or non-fused aromatic or heteroaromatic nuclei.

Further disclosed herein is a multi-compartment device comprising at least one compartment containing at least one dye composition of the present disclosure.

Still further disclosed herein are novel compounds chosen from compounds of formulas (I) and (II), and the addition salts thereof, and comprising at least one cationic quaternary ammonium group. Also disclosed herein are dye compositions comprising at least one such compound.

The compositions of the present disclosure, in at least one embodiment, produce a rapid coloration of keratin fibers that may be chromatic and fast with respect to various external factors, such as shampooing.

The compositions disclosed herein, in at least one embodiment, are clean coloration products, i.e., products that do not stain: the coloration product applied to the keratin fibers is colorless, the coloration develops in the keratin fibers, and the rinsing water is clear. As a result, the application of this coloring product may not result in any soiling.

The compounds with an open ring of formula (II) may be obtained, for example, by opening the heterocycle formed by N, Y, and Z in the compounds of formula (I) under the effect of a stimulus such as light, an electrical current, heat, the addition of an acidifying and/or basifying agent, the addition of solvent, and an electromagnetic radiation. The compounds of formula (I) are colorless or weakly colored and the corresponding compounds of formula (II) in which the heterocycle is open are colored and coloring species. In the suitable dyeing medium, an equilibrium is established between the colored species and the uncolored species, which depends on various factors such as the solvent, the acidifying and/or basifying agents present in the medium, and the temperature, and which may be represented by the following scheme:

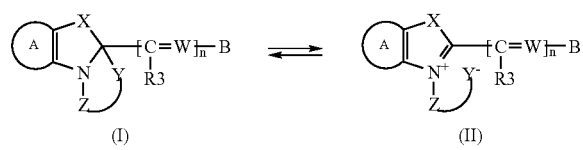

(I)  (II)

When the compounds useful in the context of the present disclosure are applied to the keratin fibers in their colorless form, the coloration is developed on the keratin fibers.

As used herein, the term "heteroaromatic nucleus" means an aromatic nucleus comprising at least one heteroatom chosen, for example, from nitrogen, sulfur, oxygen, and phosphorus.

As used herein, the term "fused" means at least two conjoined rings with at least two atoms in common.

Halo radicals, as the term is used herein, include halogen atoms chosen from chlorine, bromine, iodine, and fluorine.

As used herein, the term "alkyl radical" (alk) means a linear or branched radical, for example, methyl, ethyl, n-propyl, isopropyl, n-butyl, and tert-butyl radicals. An alkoxy radical is an alk-O— radical; a mono- or dialkylamino radical is a radical —N(alk)$_n$ with n=1 or 2; an alkylcarbonyl radical is an alk-CO— radical; an alkoxycarbonyl radical is an alk-O—CO— radical; and an alkylcarbonylalkyl radical is an alk-CO-alk- radical, wherein in each of these definitions the alkyl radical is as defined above.

A substituted alkyl radical is a monosubstituted or polysubstituted alkyl. For example, a hydroxyalkyl or an aminoalkyl is an alkyl that may be substituted with at least one group chosen from hydroxyl and amino groups, respectively.

As used herein, the term "aryl radical" (ar) means a carbon-based radical derived from fused or non-fused benzene compounds, for example, phenyl, anthracenyl, and naphthyl.

Examples of aromatic or non-aromatic 5- or 6-membered rings include 1,3-cyclopentadiene, benzene, cyclopentane, and cyclobutane.

Compounds useful in the context of the present disclosure may be neutralized with a negative or positive counterion when they are charged. The negative counterions may be chosen, for example, from halides such as a chloride, bromide, iodide, and fluoride, perchlorate, p-methylbenzenesulfonate, tetrafluoroborate, sulfate, alkyl sulfate, toluenesulfonate, and sulfonate. The positive counterions may be chosen, for instance, from alkali metal and alkaline-earth metal salts, such as sodium and potassium ions.

According to one embodiment of the present disclosure, A may be chosen from benzene, anthracene, naphthalene, and quinoline nuclei.

According to another embodiment of the present disclosure, A may be unsubstituted or substituted with at least one group chosen from halo radicals, $C_1$-$C_6$ alkyl radicals, $C_1$-$C_6$ alkoxy radicals, $C_1$-$C_6$ alkylsulfonyl radicals (—$SO_2$-alkyl), $C_1$-$C_6$ alkylsulfonate radicals (—$SO_3$-alkyl), cyano radicals, trifluoromethyl radicals, $C_1$-$C_6$ alkylcarbonyl radicals, trifluoromethylsulfonyl radicals (—$SO_2$—$CF_3$), trifluoromethylcarbonyl radicals, phenylsulfonyl radicals (—$SO_2$-Ph), phenylsulfonate radicals (—$SO_3$-Ph), phenylcarbonyl radicals, nitro radicals, $C_1$-$C_6$ alkoxycarbonyl radicals, phosphonyl radicals (—$PO(OH)_2$), phosphonyl($C_1$-$C_6$)alkyl radicals (-alkyl-$PO(OH)_2$), hydroxyl radicals, amino radicals, di($C_1$-$C_6$)alkylamino radicals, (hydroxy($C_1$-$C_6$)alkyl)amino radicals, di(hydroxy($C_1$-$C_6$)alkyl)amino radicals, (amino($C_1$-$C_6$)alkyl)amino radicals, di(amino($C_1$-$C_6$)alkyl)amino radicals, (hydroxy($C_1$-$C_6$)alkyl)(($C_1$-$C_6$)alkyl)amino radicals, (amino($C_1$-$C_6$)alkyl)(($C_1$-$C_6$)alkyl)amino radicals, (amino($C_1$-$C_6$)alkyl)(hydroxy($C_1$-$C_6$)alkyl)amino radicals, hydroxy($C_1$-$C_6$)alkyl radicals, amino($C_1$-$C_6$)alkyl radicals, (($C_1$-$C_6$)alkyl)amino($C_1$-$C_6$)alkyl radicals, di(($C_1$-$C_6$)alkyl)-amino($C_1$-$C_6$)alkyl radicals, (hydroxy($C_1$-$C_6$)alkyl)amino($C_1$-$C_6$)alkyl radicals, di(hydroxy($C_1$-$C_6$)alkyl)amino($C_1$-$C_6$)alkyl radicals, (amino($C_1$-$C_6$)alkyl)amino($C_1$-$C_6$)alkyl radicals, di(amino($C_1$-$C_6$)alkyl)amino($C_1$-$C_6$)alkyl radicals, (($C_1$-$C_6$)

alkyl)(hydroxy($C_1$-$C_6$)alkyl)amino-($C_1$-$C_6$)alkyl radicals, (amino($C_1$-$C_6$)alkyl)(($C_1$-$C_6$)alkyl)amino radicals, (hydroxy($C_1$-$C_6$)alkyl)(($C_1$-$C_6$)alkyl)amino($C_1$-$C_6$)alkyl radicals; phenyl($C_1$-$C_6$)alkyl radicals optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals, cationic quaternary ammonium groups, $C_1$-$C_6$ alkyl radicals substituted with a cationic quaternary ammonium group, carboxyl radicals, ($C_1$-$C_6$)alkyl radicals substituted with a carboxyl radical, thio radicals, thio($C_1$-$C_6$)alkyl radicals, sulfonate radicals (—$SO_3^-$), ($C_1$-$C_6$)alkyl radicals substituted with a sulfonate radical, ($C_1$-$C_6$)alkylcarbonyl ($C_1$-$C_6$)alkyl radicals, di(halo($C_1$-$C_6$)alkyl)amino radicals, acetamido radicals, aryloxy radicals, aryloxy($C_1$-$C_6$)alkyl radicals, ethenyl radicals (—CH=$CH_2$), ethenylcarbonyl radicals (—CO—CH=$CH_2$); wherein two adjacent groups may optionally form an aromatic or heteroaromatic ring, which is optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals, or a —O—$C_mH_{2m}$—O— ring wherein m is an integer equal to 1 or 2. In at least one embodiment, A is optionally substituted with at least one group chosen from ($C_1$-$C_6$)alkylsulfonyl radicals; pyridinium groups, and imidazolium groups, which are optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals; tri-($C_1$-$C_6$) alkylammonium groups; and sulfonate radicals. For example, A may be substituted with an entity chosen from methylsulfonyl radicals; 1-methyl-2-pyridinium groups; imidazolium groups; trimethylammonium groups; and sulfonate radicals.

According to one embodiment of the present disclosure, X may be chosen from group $CR_1R_2$ groups.

According to another embodiment, $R_1$ and $R_2$ may be chosen from $C_1$-$C_6$ alkyl radicals. For example, $R_1$ and $R_2$ may be chosen from methyl and ethyl radicals.

In yet another embodiment of the present disclosure, $R_3$ may be hydrogen.

According to a further embodiment, W may be chosen from $CR_4$ groups.

According to a still further embodiment of the present disclosure, $R_4$ may be hydrogen.

In another embodiment, Y may be oxygen.

According to yet another embodiment of the present disclosure, Z may be chosen from —$C_pH_{2p}$— groups, wherein p is an integer ranging from 2 to 4, which is optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals. For example, Z may be chosen from —$C_2H_4$— groups.

In a further embodiment, n may be equal to 1 or 2.

According to a still further embodiment of the present disclosure, B may be chosen from benzene, carbazole, and indole nuclei.

According to another embodiment, B may be optionally substituted with at least one group chosen from halo radicals; $C_1$-$C_6$ alkyl radicals; $C_1$-$C_6$ alkoxy radicals; cyano radicals; trifluoromethyl radicals; $C_1$-$C_6$ alkylcarbonyl radicals; trifluoromethylsulfonyl radicals; trifluoromethylcarbonyl radicals; phenylsulfonyl radicals; phenylcarbonyl radicals; phenyl radicals optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals; acylamino radicals; hydroxyl radicals; amino radicals; di(($C_1$-$C_6$)alkyl)amino radicals; hydroxy($C_1$-$C_6$)alkylamino radicals; di(hydroxy($C_1$-$C_6$)alkyl)amino radicals; (amino ($C_1$-$C_6$)alkyl)amino radicals; di(amino($C_1$-$C_6$)alkyl)amino radicals; (($C_1$-$C_6$)alkyl)(hydroxy($C_1$-$C_6$)alkyl)amino radicals; (amino($C_1$-$C_6$)alkyl)(($C_1$-$C_6$)alkyl)amino radicals; (amino($C_1$-$C_6$)alkyl)(hydroxy($C_1$-$C_6$)alkyl)amino radicals; hydroxy($C_1$-$C_6$)alkyl radicals; amino($C_1$-$C_6$)alkyl radicals; ($C_1$-$C_6$)alkylamino($C_1$-$C_6$)alkyl radicals; di(($C_1$-$C_6$)alkyl)amino($C_1$-$C_6$)alkyl radicals; (hydroxy($C_1$-$C_6$)alkyl)amino ($C_1$-$C_6$)alkyl radicals, di(hydroxy($C_1$-$C_6$)alkyl)amino($C_1$-$C_6$)alkyl radicals; amino($C_1$-$C_6$)alkylamino($C_1$-$C_6$)alkyl radicals; di(amino($C_1$-$C_6$)alkyl)amino($C_1$-$C_6$)alkyl radicals; (($C_1$-$C_6$)alkyl)(hydroxy($C_1$-$C_6$)alkyl)amino($C_1$-$C_6$)alkyl radicals; (($C_1$-$C_6$)alkyl)(amino($C_1$-$C_6$)alkyl)amino radicals; (hydroxy($C_1$-$C_6$)alkyl)(($C_1$-$C_6$)alkyl)amino($C_1$-$C_6$)alkyl radicals; phenyl($C_1$-$C_6$)alkyl radicals optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals; cationic quaternary ammonium groups; ($C_1$-$C_6$)alkyl radicals substituted with a cationic quaternary ammonium group; carboxyl radicals, ($C_1$-$C_6$)alkyl radicals substituted with a carboxyl radical, thio radicals; thio($C_1$-$C_6$)alkyl radicals; sulfonate radicals; ($C_1$-$C_6$)alkyl radicals substituted with a sulfonate radical; ($C_1$-$C_6$)alkylcarbonyl($C_1$-$C_6$)alkyl radicals; di(halo($C_1$-$C_6$)alkyl)amino radicals; acetamido radicals; aryloxy radicals; aryloxy($C_1$-$C_6$) alkyl radicals; ethenyl radicals, ethenylcarbonyl radicals, $NR_6R_7$ groups, wherein $R_6$ and $R_7$ may form, together with the nitrogen atom to which they are attached, a non-aromatic $C_5$, $C_6$ or $C_7$ ring, optionally interrupted with at least one heteroatom chosen, for example, from nitrogen, oxygen, and sulfur; alkylene chains optionally comprising at least one atom chosen from oxygen and sulfur and optionally ending with a group chosen from cyano, $C_1$-$C_6$ alkylsulfonyl, and $C_1$-$C_6$ alkylcarbonyl groups; wherein two adjacent groups of B may optionally form an aromatic or heteroaromatic ring, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals, or —O—$C_rH_{2r}$—O— ring, wherein r is an integer equal to 1 or 2. In at least one embodiment, B may be optionally substituted with at least one group chosen from hydroxyl radicals; amino radicals; di(($C_1$-$C_6$)alkyl)amino radicals; $C_1$-$C_6$ alkyl radicals; acetamido radicals; pyridinium groups; and tri($C_1$-$C_6$)alkylammonium groups. For example, B may be substituted with at least one entity chosen from hydroxyl radicals; amino radicals; dimethylamino radicals; ethyl radicals; acetamido radicals; pyridinium groups; and trimethylammonium groups.

The cationic quaternary ammonium groups may be chosen, for example, from trialkylammonium, oxazolium, thiazolium, imidazolium, pyrazolium, pyridinium, pyrrolium, triazolium, isoxazolium, isothiazolium, pyrimidinium, pyrazinium, triazinium, pyridazinium, indolium, quinolinium, and isoquinolinium groups, which may be substituted or unsubstituted, and may be linked to the nucleus A or to the nucleus B via any of their unsubstituted carbon atoms.

Examples of compounds of formula (I) include, but are not limited to, 9a-[2-[4-(dimethylamino)phenyl]-1,3-butadienyl]-2,3,9,9a-tetrahydro-9,9-dimethyloxazolo[3,2-a]indole-7-carboxylic acid; [9a-[2-[4-(dimethylamino)phenyl] ethenyl]-2,3,9,9a-tetrahydro-9,9-dimethyloxazolo[3,2-a] indol-7-yl]phosphonic acid; 4-[2-(9,9-diethyl-2,3-dihydro- 7-methoxyoxazolo[3,2-a]indol-9a(9H)-yl)ethenyl]-N,N-diethylbenzenamine; [3-[9a-[2-[4-(dimethylamino)phenyl]ethenyl]-2,3,9,9a-tetrahydro-9,9-dimethyloxazolo[3,2-a]indol-7-yl]propyl]phosphonic acid; 4-[2-(2,3-dihydro-9,9-dimethyloxazolo[3,2-a]indol-9a(9H)-yl)ethenyl]-N-methyl-N-phenylbenzenamine; 4-[2-(2,3-dihydro-9,9-dimethyloxazolo[3,2-a]indol-9a(9H)-yl)ethenyl]-3-ethoxy-N,N-diethylbenzenamine; 4-[2-(2,3-dihydro-9,9-dimethyloxazolo[3,2-a]indol-9a(9H)-yl)ethenyl]-N-ethyl-N-(2-methylpropyl)benzenamine; 4-[2-(2,3-dihydrooxazolo[3,2-a]indol-9a(9H)-yl)ethenyl]-N,N-dimethylbenzenamine; 4-[4-(2,3-dihydro-7,9,9-trimethyloxazolo[3,2-a]indol-9a(9H)-yl)-1,3-butadienyl]-N,N-dimethylbenzenamine; 4-[4-(2,3-dihydro-9,9-dimethyl-7-nitrooxazolo[3,2-a]indol-9a(9H)-yl)-1,3-butadienyl]-N,N-dimethylbenzenamine; 9a-[4-[4-(dimethylamino)phenyl]-1,3-butadienyl]-2,3,9,9a-tetrahydro-9,9-dimethyloxazolo[3,2-a]indole-7-carbonitrile; 9a-[2-[4-(dimethylamino)phenyl]ethenyl]-2,3,9,9a-tetrahydro-9,9-dimethyloxazolo[3,2-a]indole-7-carbonitrile; 4-[2-(2,3-dihydro-9,9-dimethyloxazolo[3,2-a]indol-9a(9H)-yl)ethenyl]-N,N-dimethylbenzenamine; 9a-[2-[4-(dimethylamino)phenyl]ethenyl]-2,3,9,9a-tetrahydro-9,9-dimethyloxazolo[3,2-a]indole-7-sulfonic acid methyl ester; N,N-bis(2-chloroethyl)-4-[2-(2,3-dihydro-9,9-dimethyloxazolo[3,2-a]indol-9a(9H)-yl)ethenyl]benzenamine; 9a-[2-[4-(dimethylamino)phenyl]ethenyl]-9,9a-dihydro-9,9-dimethyl-7-(octylsulfonyl)oxazolo[3,2-a]-indol-2(3H)-one; 9a-[2-[4-(dimethylamino)phenyl]ethenyl]-9,9a-dihydro-9,9-dimethyl-7-(phenylsulfonyl)oxazolo[3,2-a]indol-2(3H)-one; 9a-[2-[4-(dimethylamino)phenyl]-1-methylethenyl]-9,9a-dihydro-9,9-dimethyl-7-(methylsulfonyl)oxazolo[3,2-a]indol-2(3H)-one; 9a-[2-[4-(dimethylamino)phenyl]ethenyl]-9,9a-dihydro-9,9-dimethyl-7-(methylsulfonyl)oxazolo[3,2-a]indol-2(3H)-one; 4-[2-[2,3-dihydro-9,9-dimethyl-7-(methyl-sulfonyl)oxazolo[3,2-a]indol-9a(9H)-yl]ethenyl]-N,N-dimethylberizenamine; 4-[2-[9-(ethoxymethyl)-2,3-dihydro-9-methyl-7-(methylsulfonyl)oxazolo[3,2-a]indol-9a(9H)-yl]ethenyl]-N,N-dimethylbenzenamine; 4-[2-[2,3-dihydro-2,9,9-trimethyl-7-(methylsulfonyl)oxazolo[3,2-a]indol-9a(9H)-yl]ethenyl]-N,N-dimethylbenzenamine; 4-[2-[2,3-dihydro-9,9-dimethyl-7-(methylsulfonyl)oxazolo[3,2-a]indol-9a(9H)-yl]-1-propenyl]-N,N-dimethylbenzenamine; N,N-dibutyl-4-[2-[2,3-dihydro-9,9-dimethyl-7-(methylsulfonyl)oxazolo[3,2-a]indol-9a(9H)-yl]ethenyl]benzenamine; 4-[2-[2,3-dihydro-9,9-dimethyl-7-(phenylsulfonyl)oxazolo[3,2-a]indol-9a(9H)-yl]ethenyl]-N,N-dimethyl; 4-[2-[2,3-dihydro-9,9-dimethyl-7-(octylsulfonyl)oxazolo[3,2-a]indol-9a(9H)-yl]ethenyl]-N,N-dimethylbenzenamine; N-[4-[2-[7-(butylsulfonyl)-2,3-dihydro-9,9-dimethyloxazolo[3,2-a]indol-9a(9H)-yl]ethenyl]phenyl]acetamide; 4-[2-[7-(butylsulfonyl)-2,3-dihydro-9,9-dimethyloxazolo[3,2-a]indol-9a(9H)-yl]ethenyl]-N,N-dimethylbenzenamine; 4-[4-[2,3-dihydro-9,9-dimethyl-7-(methylsulfonyl)oxazolo[3,2-a]indol-9a(9H)-yl]-1,3-butadienyl]N,N-dimethylbenzenamine; 9a-[2-[4-(dimethylamino)phenyl]ethenyl]-2,3,9,9a-tetrahydro-9-methyloxazolo[3,2-a]indole-9-ethanol; 4-[2-(9,9-diethyl-2,3-dihydrooxazolo[3,2-a]indol-9a(9H)-yl)ethenyl]-N,N-dimethylbenzenamine; 4-[2-[2,3-dihydro-9-methyl-9-(2-phenoxyethyl)oxazolo[3,2-a]indol-9a(9H)-yl]ethenyl]-N,N-dimethylbenzenamine; 4-[2-[9-(ethoxymethyl)-2,3-dihydro-9-methyloxazolo[3,2-a]indol-9a(9H)-yl]ethenyl]-N,N-dimethylbenzenamine; 4-[2-(11,11-dimethylbenz[e]oxazolo[3,2-a]indol-10a(11H)-yl)ethenyl]-N,N-dimethylbenzenamine; 4-[2-(7-methoxy-9,9-dimethyloxazolo[3,2-a]indol-9a(9H)-yl)ethenyl]-N,N-dimethylbenzenamine; 4-[2-(9,9-dimethyloxazolo[3,2-a]indol-9a(9H)-yl)ethenyl]-N,N-dimethylbenzenamine; 9a-[2-[4-(dimethylamino)phenyl]ethenyl]-3-ethyl-9,9a-dihydro-9,9-dimethyloxazolo[3,2-a]indol-2(3H)-one; 7-choro-9a-[2-[4-(dimethylamino)phenyl]ethenyl]-9,9a-dihydro-3,9,9-trimethyloxazolo[3,2-a]indol-2(3H)-one; 9a-[2-[4-(dibutylamino)phenyl]ethenyl]-9,9a-dihydro-9,9-dimethyloxazolo[3,2-a]indol-2(3H)-one; 9a-[2-[4-(dimethylamino)phenyl]ethenyl]-9,9a-dihydro-9-(2-hydroxyethyl)-9-methyloxazolo[3,2-a]indol-2(3H)-one; 9a-[2-[4-(dimethylamino)phenyl]-1-propenyl]-9,9a-dihydro-9,9-dimethyloxazolo[3,2-a]indol-2(3H)-one; 9,9a-dihydro-7,9,9-trimethyl-9a-[2-(4-nitrophenyl)ethenyl]oxazolo[3,2-a]indol-2(3H)-one; N-[4-[2-(2,3-dihydro-9,9-dimethyl-2-oxooxazolo[3,2-a]indol-9a(9H)-yl)ethenyl]phenyl]acetamide; 9a-[2-[4-(dimethylamino)-phenyl]ethenyl]-9,9a-dihydro-6-methoxy-9,9-dimethyloxazolo[3,2-a]indol-2(3H)-one; 9a-[2-[4-(dimethylamino)phenyl]ethenyl]-2,3,9,9a-tetrahydro-9,9-dimethyl-2-oxooxazolo[3,2-a]indole-7-carboxylic acid ethyl ester; 9a-[2-[4-(dimethylamino)phenyl]ethenyl]-9,9a-dihydro-7,9,9-trimethyloxazolo[3,2-a]indol-2(3H)-one; 10a-[2-[4-(dimethylamino)phenyl]ethenyl]-10a,11-dihydro-11,11-dimethylbenz[e]oxazolo[3,2-a]indol-9(8H)-one; 9,9a-dihydro-9,9-dimethyl-9a-[2-(4-nitrophenyl)ethenyl]oxazolo[3,2-a]indol-2(3H)-one; 7-chloro-9a-[2-[4-(dimethylamino)phenyl]ethenyl]-9,9-dihydro-9,9-dimethyloxazolo[3,2-a]indol-2(3H)-one; 9a-[2-[4-(dimethylamino)phenyl]ethenyl]-9,9a-dihydro-9,9-dimethyloxazolo[3,2-a]indol-2(3H)-one; 4-[2-(7-chloro-2,3-dihydro-9,9-dimethyloxazolo[3,2-a]indol-9a(9H)-yl)ethenyl]-N,N-dimethylbenzenamine; 4-[2-(2,3-dihydro-9,9-dimethyloxazolo[3,2-a]indol-9a(9H)-yl)ethenyl]-N,N-dimethylbenzenamine; 4-[2-(7-chloro-2,3-dihydro-2,9,9-trimethyloxazolo[3,2-a]indol-9a(9H)-yl)ethenyl]-N,N-dimethylbenzenamine; 4-[2-(2,3-dihydro-9,9-dimethyloxazolo[3,2-a]indol-9a(9H)-yl)-1-methylethenyl]-N,N-dimethylbenzenamine; 4-[2-(2,3-dihydro-9,9-dimethyloxazolo[3,2-a]indol-9a(9H)-yl)ethenyl]-N,N-diethylbenzenamine; 2,3,9,9a-tetrahydro-7-methoxy-9,9-dimethyl-9a-[2-(4-nitrophenyl)ethenyl]oxazolo[3,2-a]indole; 4-[2-(2,3-dihydro-9,9-dimethyl-7-nitrooxazolo[3,2-a]indol-9a(9H)-yl)ethenyl]-N,N-dimethylbenzenamine; N,N-dibutyl-4-[2-(2,3-dihydro-9,9-dimethyloxazolo[3,2-a]indol-9a(9H)-yl)ethenyl]benzenamine; 2,3,9,9a-tetrahydro-9,9-dimethyl-7-nitro-9a-[2-(4-nitrophenyl)-ethenyl]oxazolo[3,2-a]indole; 7-chloro-2,3,9,9a-tetrahydro-9,9-dimethyl-9a-[2-(4-nitrophenyl)ethenyl]oxazolo[3,2-a]indole; 4-[2-(2,3-dihydro-7-iodo-9,9-dimethyloxazolo[3,2-a]indol-9a(9H)-yl)ethenyl]-N,N-dimethylbenzenamine; 4-[2-(2,3-dihydro-5-methoxy-9,9-dimethyloxazolo[3,2-a]indol-9a(9H)-yl)ethenyl]-N,N-dimethylbenzenamine; 4-[2-(2,3-dihydro-7-methoxy-9,9-dimethyloxazolo[3,2-a]indol-9a(9H)-yl)ethenyl]-N,N-dimethylbenzenamine; 4-[4-(2,3-dihydro-9,9-dimethyloxazolo[3,2-a]indol-9a(9H)-yl)-1,3-butadienyl]-N,N-diethylbenzenamine; 4-[4-(7-chloro-2,3-dihydro-9,9-dimethyloxazolo[3,2-a]indol-9a(9H)-yl)-1,3-butadienyl]-N,N-dimethylbenzenamine; 4-[4-(2,3-dihydro-9,9-dimethyloxazolo[3,2-a]indol-9a(9H)-yl)-1,3-butadienyl]-N,N-dimethylbenzenamine; 4-[4-(2,3-dihydro-7-methoxy-9,9-dimethyloxazolo[3,2-a]indol-9a(9H)-yl)-1,3-butadienyl]-N,N-dimethylbenzenamine; 2,3,9,9a-tetrahydro-7,9,9-trimethyl-9a-[2-(4-nitrophenyl)ethenyl]oxazolo[3,2-a]indole; N-[4-[2-(2,3-dihydro-9,9-dimethyloxazolo[3,2-a]indol-9a(9H)-yl)ethenyl]phenyl]acetamide; 4-[2-(2,3-dihydro-6-methoxy-9,9-dimethyloxazolo[3,2-a]indol-9a(9H)-yl)ethenyl]-N,N-dimethylbenzenamine; 4-[2-(8,9-dihydro-11,11-dimethylbenz[e]oxazolo[3,2-a]indol-10a(11H)-yl)ethenyl]-N,N-dimethylbenzenamine; 4-[2-(2,3- dihydro-7,9,9-trimethyloxazolo[3,2-a]indol-9a(9H)-yl)ethenyl]-N,N-dimethylbenzenamine; 2,3,9,9a-tetra-hydro-9,9-dimethyl-9a-[2-(4-nitrophenyl)ethenyl]oxazolo[3,2-a]indole; 9,9a-dihydro-9,9-dimethyl-9a-[2-(9-methyl-9H-carbazol-3-yl)ethenyl]-7-(methylsulfonyl)oxazolo[3,2-a]indol-2(3H)-one; 9a-[2-(9-hexyl-9H-carbazol-3-yl)ethenyl]-2,3,9,9a-tetrahydro-9,9-dimethyl-7-(phenylsulfonyl)oxazolo[3,2-a]indole; 2,3,9,9a-tetrahydro-9,9-dimethyl-7-(methylsulfonyl)-9a-[2-(9-octyl-9H-carbazol-3-yl)ethenyl]oxazolo[3,2-a]indole; 9a-[2-(9-butyl-6-methoxy-9H-carbazol-3-yl)ethenyl]-2,3,9,9a-tetrahydro-9,9-dimethyloxazolo[3,2-a]indole-7-carboxylic acid ethyl ester; 9a-[2-(9-ethyl-9H-carbazol-3-yl)ethenyl]-2,3,9,9a-tetrahydro-9,9-dimethyloxazolo[3,2-a]indole-7-sulfonic acid methyl ester; 3-chloro-6-[2-[2,3-dihydro-9,9-dimethyl-7-(methylsulfonyl)oxazolo[3,2-a]indol-9a(9H)-yl]ethenyl]-9-octyl-9H-carbazole; 3-[2-[2,3-dihydro-9,9-dimethyl-7-(methylsulfonyl)oxazolo[3,2-a]indol-9a(9H)-yl]ethenyl]-9-methyl-9H-carbazole; 3-[2-[9-(2-ethoxyethyl)-2,3-dihydro-9-methyl-7-(methylsulfonyl)oxazolo[3,2-a]indol-9a(9H)-yl]ethenyl]-9H-carbazole; 9a-[2-(9-hexyl-9H-carbazol-3-yl)ethenyl]-2,3,9,9a-tetrahydro-9-(2-hydroxyethyl)-9-methyloxazolo[3,2-a]indole-7-carboxylic acid ethyl ester; 2,3,9,9a-tetrahydro-9,9-dimethyl-9a-[2-(9-octyl-9H-carbazol-3-yl)ethenyl]oxazolo[3,2-a]indole-7-carboxylic acid ethyl ester; 9a-[2-(9-butyl-9H-carbazol-3-yl)ethenyl]-2,3,9,9a-tetrahydro-9,9-dimethyloxazolo[3,2-a]indole-7-carboxylic acid ethyl ester; 2,3,9,9a-tetrahydro-9,9-dimethyl-9a-[2-(9-methyl-9H-carbazol-3-yl)ethenyl]oxazolo[3,2-a]indole-7-carboxylic acid ethyl ester; 9a-[2-(9-butyl-6-ethoxy-9H-carbazol-3-yl)ethenyl]-2,3,9,9a-tetrahydro-N,N,9,9-tetramethyloxazolo[3,2-a]indol-7-amine; 2,3,9,9a-tetrahydro-9-methyl-9a-[2-(9-methyl-9H-carbazol-3-yl)ethenyl]oxazolo[3,2-a]indole-9-ethanol; 9a-[2-(9-butyl-9H-carbazol-3-yl)ethenyl]-2,3,9,9a-tetrahydro-N,N,9,9-tetramethyloxazolo[3,2-a]indol-7-amine; 3-[2-(2,3-dihydro-6-methoxy-9,9-dimethyloxazolo[3,2-a]indol-9a(9H)-yl)ethenyl]-9-methyl-9H-carbazole; 3-[2-(2,3-dihydro-9,9-dimethyloxazolo[3,2-a]indol-9a(9H)-yl)-1-propenyl]-9-methyl-9H-carbazole; 3-[2-(7-chloro-2,3-dihydro-9,9-dimethyloxazolo[3,2-a]indol-9a(9H)-yl)-ethenyl]-9-methyl-9H-carbazole; 3-bromo-6-[2-(2,3-dihydro-9,9-dimethyloxazolo[3,2-a]indol-9a(9H)-yl]ethenyl]-9-ethyl-9H-carbazole; and 3-[2-(2,3-dihydro-9,9-dimethyloxazolo[3,2-a]indol-9a(9H)-yl)ethenyl]-9-methyl-9H-carbazole.

In at least one embodiment, the at least one compound of formula (I) may be chosen from:

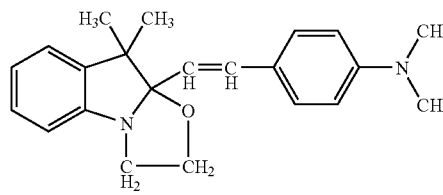
Dye 1

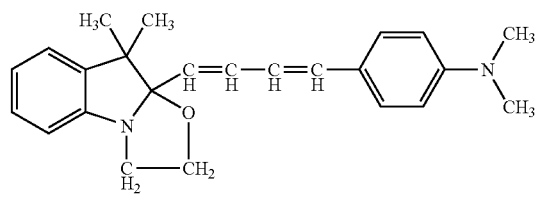
Dye 2

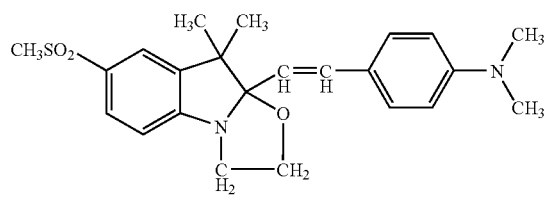
Dye 3

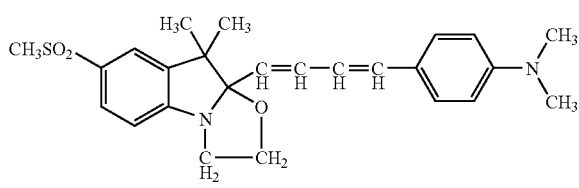
Dye 4

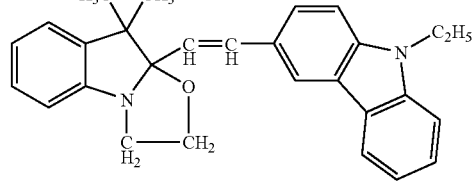
Dye 5

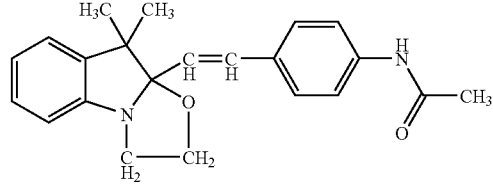
Dye 6

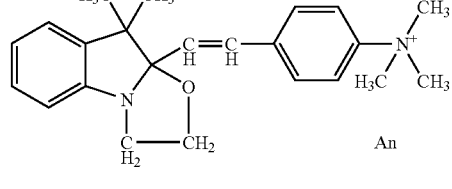
Dye 7

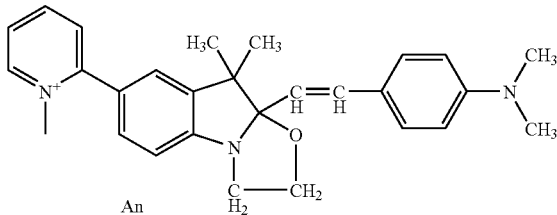
Dye 8

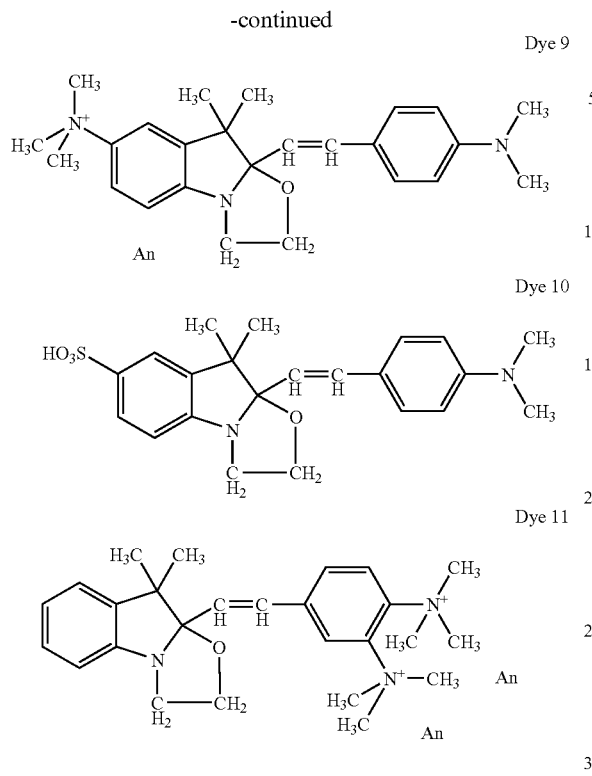
in which An, which may be identical or different, is a negative counterion chosen, for example, from halides, such as chlorides, bromides, iodides, and fluorides, perchlorates, p-methylbenzenesulfonates, tetrafluoroborates, sulfates, alkyl sulfates, toluenesulfonates, and sulfonates.
In another embodiment, the at least one compound of formula (I) may be chosen from:
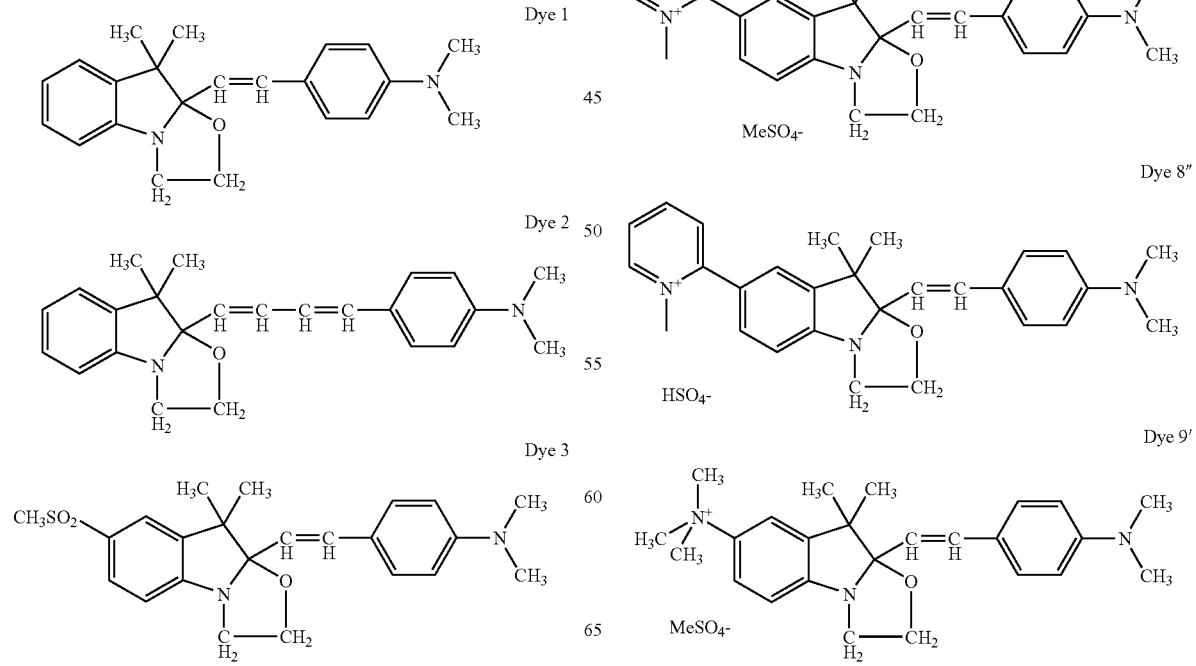
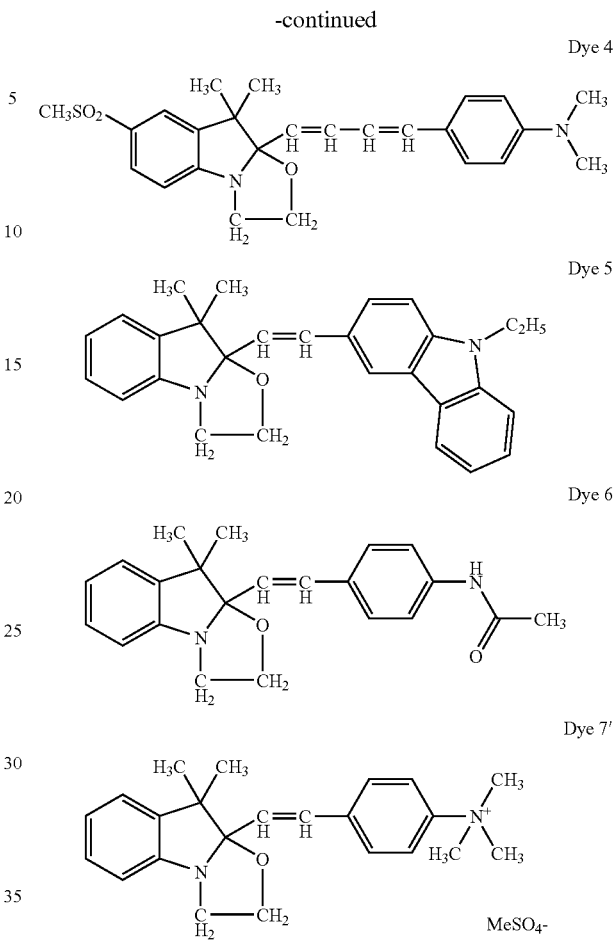

-continued

Dye 10
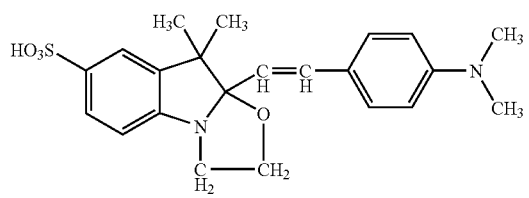

Dye 11'
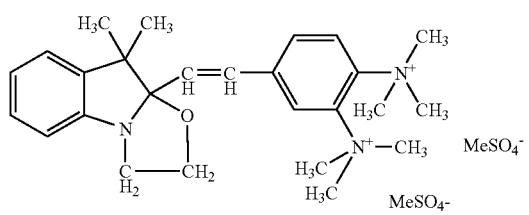

The compounds of formula (I) may be prepared, for example, according to the preparation modes as described in French Patent No. 2 285 439 and U.S. Pat. No. 4,380,629. These preparation modes may be adapted to the cationic compounds of formula (I) by adding a quaternization step. For example, the synthesis of dye 8 may be performed according to the following reaction scheme:

The at least one compound chosen from compounds of formulas (I) and (II), and the addition salts thereof, may be present in the composition in an amount ranging from 0.0001% to 10% by weight relative to the total weight of the dye composition.

The addition salts of the compounds of formulas (I) and (II) may be chosen from acid addition salts, such as hydrochlorides, hydrobromides, sulfates, methosulfates, gluconates, citrates, succinates, tartrates, lactates, tosylates, benzenesulfonates, phosphates, and acetates, and base addition salts, such as sodium hydroxide, potassium hydroxide, ammonia, amines, and alkanolamines.

The composition of the present disclosure may further comprise at least one direct dye chosen, for example, from nitrobenzene dyes, azo direct dyes, methane direct dyes, and natural dyes. These direct dyes may be chosen from nonionic, anionic, and cationic direct dyes.

The at least one direct dye may be present in the dye composition in an amount ranging from 0.001% to 20% by weight, for example, from 0.01% to 10% by weight, relative to the total weight of the dye composition.

The composition of the present disclosure may also comprise at least one oxidation dye chosen from the oxidation bases and couplers conventionally used in oxidation dyeing.

The oxidation bases may be chosen, for example, from para-phenylenediamines, bis(phenyl)alkylenediamines, para-aminophenols, bis-para-aminophenols, ortho-aminophenols, ortho-phenylenediamines, heterocyclic bases, and the addition salts thereof.

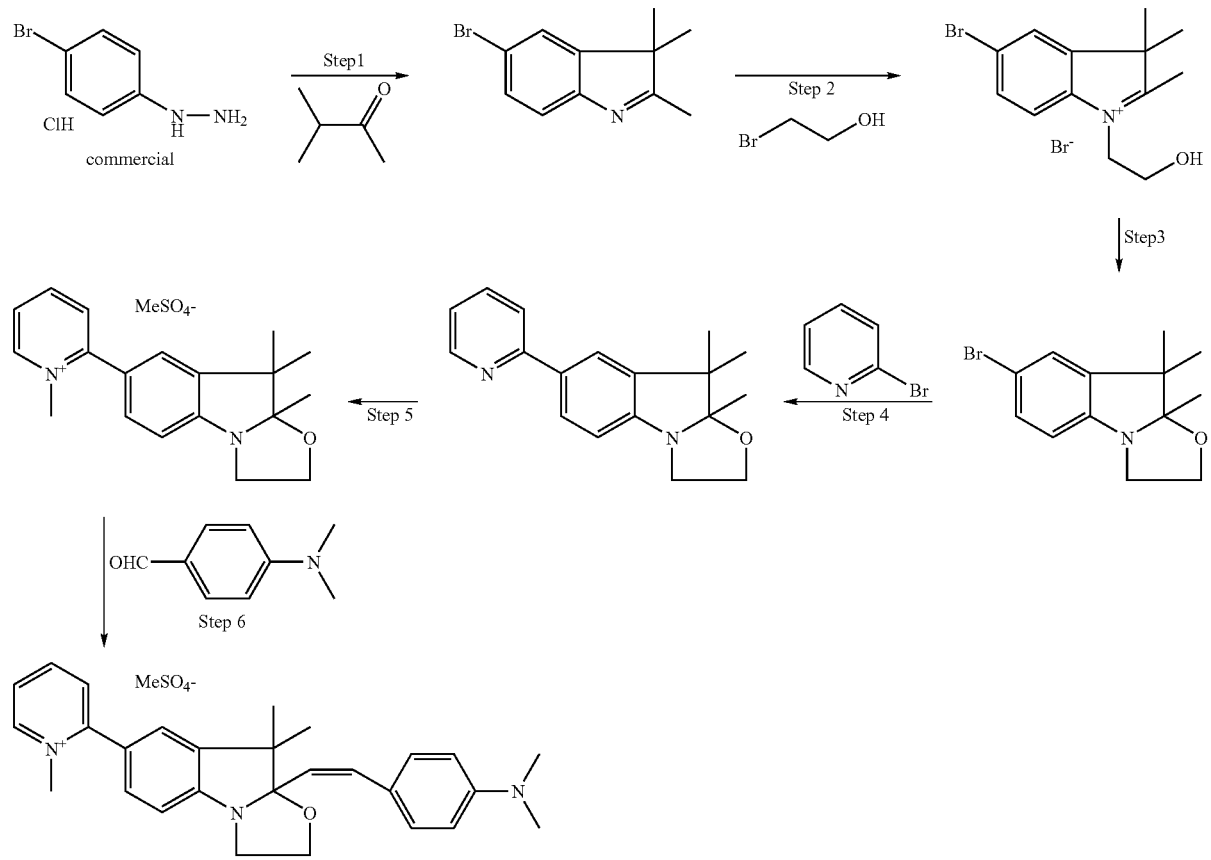

The couplers may be chosen from meta-phenylenediamines, meta-aminophenols, meta-diphenols, naphthalene-based couplers, heterocyclic couplers, and the addition salts thereof.

The at least one oxidation dye may be present in the dye composition in an amount ranging from 0.001% to 20% by weight, for example, from 0.01% to 10% by weight, relative to the total weight of the dye composition.

The composition of the present disclosure may also comprise at least one agent chosen from acidifying agents and/or basifying agents usually used in the dyeing of keratin fibers.

Examples of suitable acidifying agents include, but are not limited to, mineral acids, for instance, hydrochloric acid, nitric acid, and sulfuric acid, and organic acids, for instance, compounds comprising at least one function chosen from carboxylic acid functions, such as acetic acid, tartaric acid, citric acid, and lactic acid, sulfonic acid functions, phosphonic acid functions, and phosphoric acid functions.

Suitable basifying agents may include, for example:
basic amino acids;
alkali metal and alkaline-earth metal carbonates or bicarbonates;
silicates and metasilicates;
compounds of formula (III):

$$X(OH)_n \quad (III)$$

wherein:
when n is equal to 1, X is chosen from potassium, lithium, sodium, and ammonium ions $N^+R_8R_9R_{10}R_{11}$, wherein $R_8$, $R_9$, $R_{10}$, and $R_{11}$, which may be identical or different, are chosen from $C_2$-$C_4$ alkyl radicals; and
when n is equal to 2, X is chosen from magnesium and calcium;

for example, sodium hydroxide and potassium hydroxide;
compounds of formula (IV):

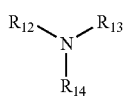

(IV)

wherein:
$R_{12}$ is chosen from hydrogen; $C_1$-$C_6$ alkyl radicals; $C_1$-$C_6$ monohydroxyalkyl radicals; and $C_2$-$C_6$ polyhydroxyalkyl radicals; and
$R_{13}$ and $R_{14}$, which may be identical or different, are chosen from hydrogen; $C_1$-$C_6$ alkyl radicals; $C_1$-$C_6$ monohydroxyalkyl radicals; and $C_2$-$C_6$ polyhydroxyalkyl radicals;

for example, ammonia and alkanolamnes such as monoethanolamine, diethanolamine, and triethanolamine, and derivatives thereof; and
compound of formula (V):

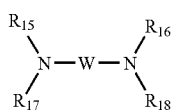

(V)

wherein:
W is a propylene residue optionally substituted with at least one entity chosen from hydroxyl group and $C_1$-$C_4$ alkyl radicals;
$R_{15}$, $R_{16}$, $R_{17}$, and $R_{18}$, which may be identical or different, are chosen from hydrogen, $C_1$-$C_4$ alkyl radicals, and $C_1$-$C_4$ hydroxyalkyl radicals.

As used herein, the term "basic amino acid" means either (i) an amino acid comprising, in addition to the amine function located a to the carboxyl group, an additional cationic (or basic) group; (ii) an amino acid comprising a cationic (or basic) side chain (hydrophilic); or (iii) an amino acid bearing a side chain comprising a nitrogenous base. These definitions are generally known and published in general biochemistry texts such as J. H. Weil (1983), pages 5 et seq., Lubert Stryer (1995), page 22, A. Lehninger (1993), pages 115-116, and de Boeck-Wesmael (1994), pages 57-59.

The basic amino acids in accordance with the present disclosure may be chosen from those of formula (D):

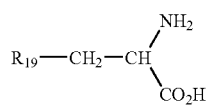

(D)

wherein $R_{19}$ is a group chosen from:

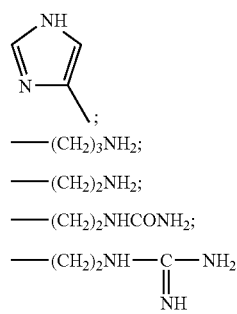

——(CH$_2$)$_3$NH$_2$;

——(CH$_2$)$_2$NH$_2$;

——(CH$_2$)$_2$NHCONH$_2$;

——(CH$_2$)$_2$NH——C——NH$_2$
               ‖
               NH

Suitable compounds of formula (D) may include, for example, histidine, lysine, ornithine, citrulline, and arginine.

The suitable dyeing medium, also known as the dye support, may be chosen from water, organic solvents, and mixtures of water and at least one organic solvent. Examples of organic solvents include, but are not limited to, ketones such as acetone; linear or branched monoalcohols and diols, which may be saturated, comprising from 2 to 10 carbon atoms, such as ethyl alcohol, isopropyl alcohol, hexylene glycol (2-methyl-2,4-pentanediol), neopentyl glycol, and 3-methyl-1,5-pentanediol; aromatic alcohols such as benzyl alcohol and phenylethyl alcohol; polyols and polyol ethers, for instance, ethylene glycol monomethyl, monoethyl, and monobutyl ether, 2-butoxyethanol, propylene glycol, and ethers thereof, for instance, propylene glycol monomethyl ether, butylene glycol, and dipropylene glycol; diethylene glycol alkyl ethers, for example, $C_1$-$C_4$ diethylene glycol alkyl ethers, for instance, diethylene glycol monoethyl ether and monobutyl ether; and mixtures thereof.

The at least one solvent may be present in the dye composition in an amount ranging from 1% to 40% by weight, for example, from 5% to 30% by weight, relative to the total weight of the dye composition.

The at least one compound chosen from the compounds of formulas (I) and (II), and the addition salts thereof, may be soluble or in dispersion in the dye support.

The composition of the present disclosure may also contain at least one adjuvant conventionally used in hair dye compositions, such as anionic, cationic, nonionic, amphoteric, and zwitterionic surfactants, and mixtures thereof; anionic, cationic, nonionic, amphoteric, and zwitterionic polymers, and mixtures thereof; mineral and organic thickeners, for example, anionic, cationic, nonionic, and amphoteric associative polymeric thickeners; antioxidants; penetrants; sequestrants; fragrances; buffers; dispersants; conditioning agents, for instance, cationic and amphoteric polymers, cations, volatile or nonvolatile, modified or non-modified silicones, chitosans and chitosan derivatives; film-forming agents; ceramides; preserving agents; and opacifiers.

The at least one adjuvant may be present in the composition in an amount for each ranging from 0.01% to 20% by weight relative to the total weight of the composition.

It is to be understood that a person skilled in the art will take care to select the at least one optional additional compound such that the advantageous properties intrinsically associated with the dye composition of the present disclosure are not, or are not substantially, adversely affected by the envisaged addition.

When the dye medium is chosen from water and mixtures of water and at least one organic solvent, the pH of the dye composition may range from 2 to 12, for example, from 3 to 11. The pH may be adjusted to the desired value by means of acidifying and/or basifying agents as defined above or standard buffer systems.

The composition of the present disclosure may be in various forms, such as liquids, creams, and gels, and any other form suitable for dyeing keratin fibers, such as human hair.

The keratin fiber dyeing process in accordance with the present disclosure comprises applying a composition of the present disclosure to the keratin fibers for a sufficient leave-on time, optionally followed by rinsing.

When the compounds of the present disclosure are applied to the keratin fibers in their colorless form, the coloration may be developed on the keratin fibers via the action of at least one external agent chosen from light, electrical current, heat, acidifying agents, basifying agents, solvents, and/or electromagnetic radiation.

When the coloration is developed by the action of heat, the keratin fibers may be heated using a hood, a hairdryer, and/or curling tongs, before and/or after the application of the dye composition.

When the coloration is developed by the action of an external agent chosen from acidifying agents, basifying agents, and solvents, this agent may be added to the dye composition at the time of use, or it may be used in a composition containing it, which is applied simultaneously with or sequentially to the dye composition.

According to one embodiment, the at least one compound disclosed herein may be applied to the keratin fibers in its colorless form and the coloration may be developed on the keratin fibers when the composition comes into contact with the keratin fibers or by virtue of a pre- or post-treatment comprising treating the keratin fibers via the action of at least one external agent chosen from light, electrical current, heat, acidifying agents, basifying agents, solvents, and electromagnetic radiation.

According to another embodiment, the dye composition may be applied in the presence of at least one oxidizing agent. In this case, simultaneous dyeing and bleaching of the keratin fibers may be performed.

The at least one oxidizing agent may be added to the dye composition at the time of use, or it may be used in an oxidizing composition containing it, which is applied simultaneously with or sequentially to the dye composition.

The at least one oxidizing agent may be chosen from hydrogen peroxide, urea peroxide, alkali metal bromates, persalts, peracids, and oxidase enzymes.

The leave-on time for the composition of the present disclosure may range from 5 minutes to 1 hour, for example, from 15 minutes to 1 hour.

The application temperature may range from room temperature to 80° C., for instance, from room temperature to 60° C.

Also disclosed herein is also a multi-compartment device comprising at least one first compartment containing at least one dye composition comprising at least one compound chosen from compounds of formulas (I) and (II), and the addition salts thereof, and, in at least one second compartment comprising at least one agent chosen from acidifying agents, basifying agents, and/or solvents, capable of opening the heterocycle present in the compounds of formula (I).

According to one embodiment, the multi-compartment device of the present disclosure may comprise at least one third compartment comprising at least one oxidizing agent.

Further disclosed herein are compounds comprising at least one cationic quaternary ammonium group such as tri($C_1$-$C_6$)alkylammonium, oxazolium, thiazolium, imidazolium, pyrazolium, pyridinium, pyrrolium, triazolium, isoxazolium, isothiazolium, pyrimidinium, pyrazinium, triazinium, pyridazinium, indolium, quinolinium, and isoquinolinium groups, which may be substituted or unsubstituted.

Still further disclosed herein is a dye composition comprising, in a suitable dyeing medium, at least one compound comprising at least one cationic quaternary ammonium group.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

Example of Synthesis

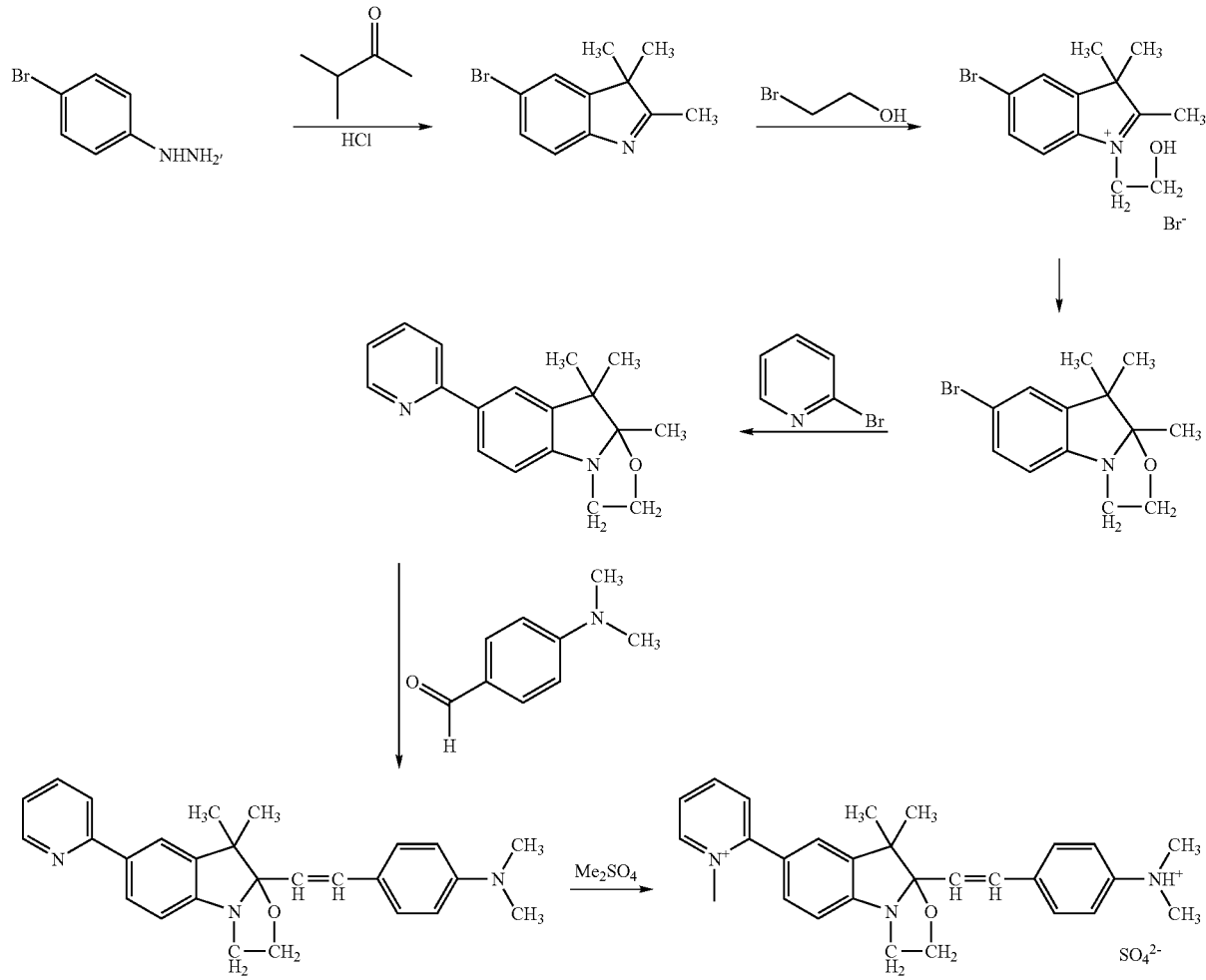

Step 1:

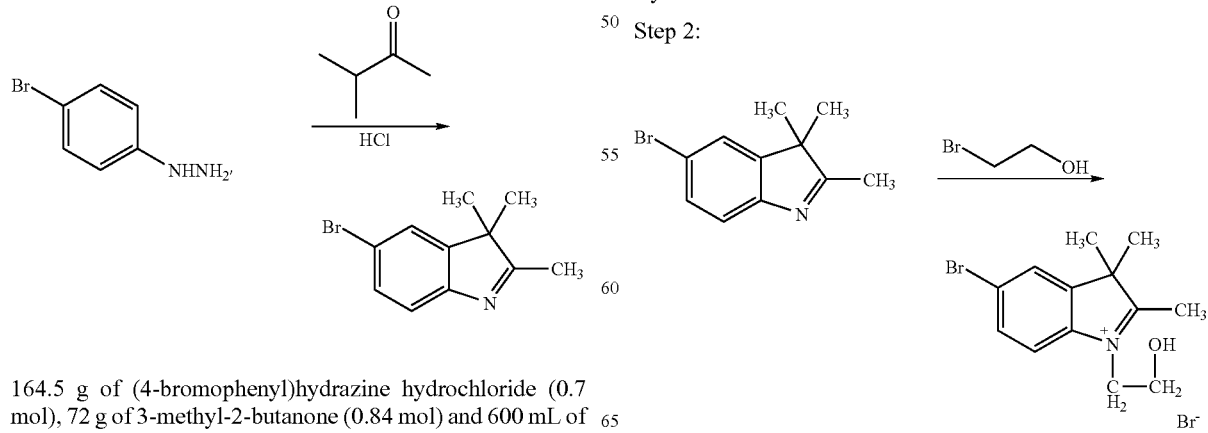

164.5 g of (4-bromophenyl)hydrazine hydrochloride (0.7 mol), 72 g of 3-methyl-2-butanone (0.84 mol) and 600 mL of ethanol were placed in a reactor, and 70 mL of 95% sulfuric acid were then added slowly. The reaction medium was brought to reflux and refluxing was continued for 5 hours. The reaction medium was then cooled to room temperature, and 470 mL of 10% sodium carbonate solution were then added to obtain a pH of 8. The mixture thus obtained was extracted with ethyl acetate. After evaporating off the ethyl acetate, 164 g of a brown-red liquid were obtained, which corresponded to a yield of 98%.

Step 2:

164 g of the product obtained in Step 1 (0.68 mol) and 83.5 g of 2-bromoethanol (0.68 mol) were placed in a reactor. The reaction medium was brought to 80° C. and stirred at this temperature for 24 hours. The reaction medium was then cooled to room temperature and filtered, and the solid obtained was then washed with acetone and dried under vacuum. 167 g of a white solid were obtained, i.e., a yield of 68%.

Step 3:

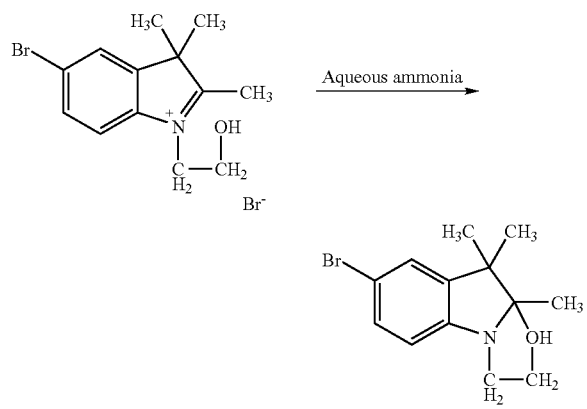

167 g of the product obtained in Step 2 (0.462 mol), 300 mL of water and 300 mL of aqueous ammonia were placed in a reactor and the reaction medium was stirred for 3 minutes. The reaction medium was then extracted with ether. After drying the organic phase over sodium sulfate, filtering, and evaporating under vacuum, 117 g of a yellow solid were obtained, which corresponded to a yield of 90.1%.

Step 4:

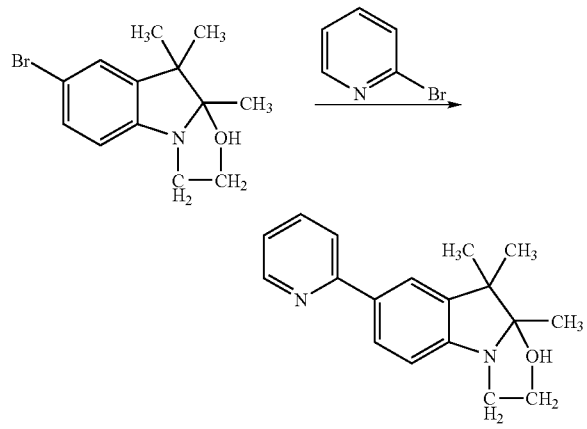

30 g of product obtained in Step 3 (107 mmol) were placed in a reactor under an inert atmosphere. 100 mL of anhydrous THF were added and the reaction medium was then brought to −90° C. 76 mL of n-butyllithium (181 mmol) were added dropwise and the reaction medium was stirred for one hour at a temperature ranging from −80 to −90° C. 107 mL of a 1M solution of $ZnCl_2$ in anhydrous THF (107 mmol) were added and the temperature of the reaction medium was returned to room temperature. Stirring was then continued for 30 minutes. 3.7 g of $Pd(PPh_3)_4$ (3.2 mmol) and 10.4 mL of 2-bromopyridine (123 mmol) were added slowly, and stirring was then continued for 2 hours at room temperature. 100 mL of water were added and the mixture was filtered. The aqueous phase was extracted with ethyl acetate. The organic phases were combined and then dried over silica gel. After filtering and evaporating under vacuum, the product obtained was purified on a chromatography column with the petroleum ether/ethyl acetate system (4/1) as eluent. 18.6 g of product were obtained, i.e., a yield of 62%.

Step 5:

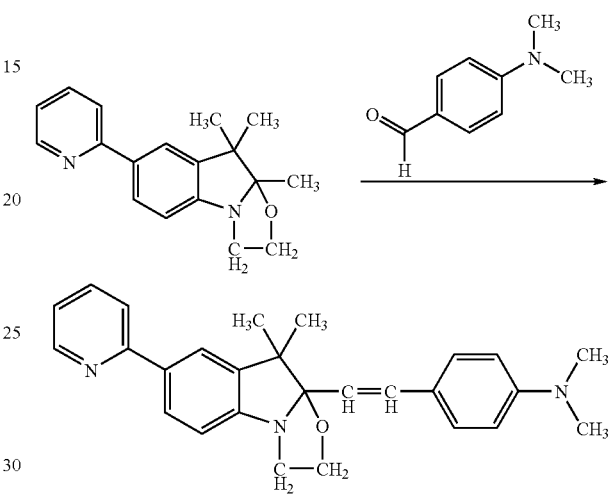

24 g of product obtained in Step 4 (0.086 mol), 80 mL of toluene, 14 g of 4-dimethylaminobenzaldehyde (0.093 mol) and 9 mL of piperidine were placed in a reactor and the reaction medium was then brought to reflux. After refluxing for 5 hours, the medium was cooled to room temperature. The product was purified by column chromatography on silica gel with the petroleum ether/ethyl acetate system (4/1) as eluent. 16.5 g of white solid were obtained, i.e., a yield of 46.7%.

Step 6:

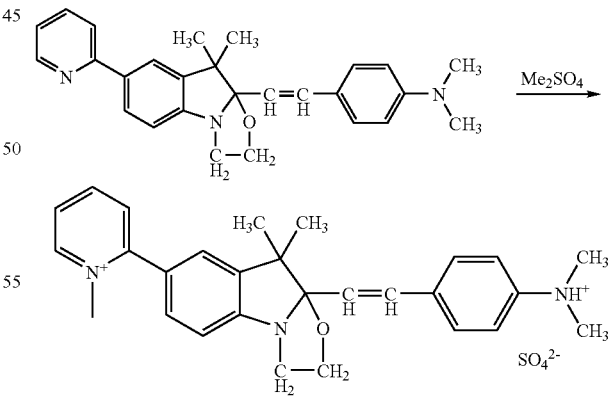

2 g of product obtained in Step 5 (4.8 mmol), 20mL of DMF, 0.24 g of 98% sulfuric acid (2.4 mmol) and 1.2 g of dimethyl sulfate (9.5 mmol) were placed in a reactor. The reaction medium was brought to 80° C. and stirred for 4 hours. The reaction medium was then cooled to room temperature, 30 mL of aqueous ammonia were added, stirring was continued for a further 30 minutes at room temperature, and 200 mL of water were then added. The product obtained was extracted with dichloromethane and purified by chromatography on silica gel with the ethyl acetate/triethylamine system (40/1) and the dichloromethane/ethanol/triethylamine system (20/1/1) as eluent. After evaporating under vacuum, the product was taken up in acetone at room temperature. The insoluble material was filtered off and then dried under vacuum. 0.5 g of green-blue solid was obtained, i.e., a yield of 19.6%.

The results obtained by $^1$H NMR were as follows:

$^1$H ((CD$_3$)$_2$SO, d): 1.81 (6H, s), 3.16 (6H, s), 3.46 (3H, s), 4.22 (2H, t), 4.73 (2H, t), 6,87 (1H, d), 7.41 (2H, m), 7.80 (1H, d), 7.92 (1H, t), 8.09 (2H, m), 8.22 (1H, dd), 8.34 (1H, d), 8.41 (1H, d), 8.69 (1H, d).

The elemental analysis was as follows:

|  | C % | H % | N % |
| --- | --- | --- | --- |
| Calculated: | 64.22 | 6.35 | 8.02 |
| Found: | 64.32 | 6.34 | 8.34 |

Examples of Dyeing

Examples 1 to 6

The dye compositions below were prepared, wherein i is an integer ranging from 1 to 6:

| Constituent | Composition i |
| --- | --- |
| Dye i* | 3 × 10$^{-3}$ mol % |
| Ethanol | 15 g |
| Benzyl alcohol | 5 g |
| Benzoic acid | 0.2 g |
| Distilled water | qs 100 g |

*Dye i was chosen from:

Dye 1
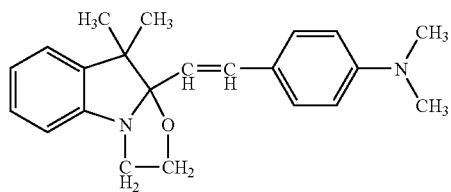

Dye 2
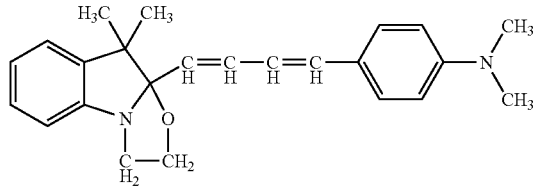

-continued

Dye 3
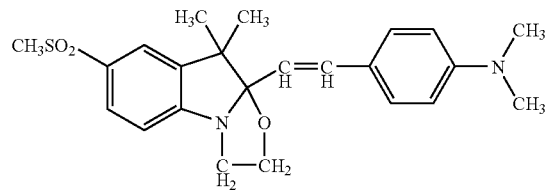

Dye 4
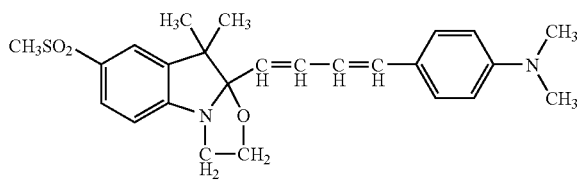

Dye 5
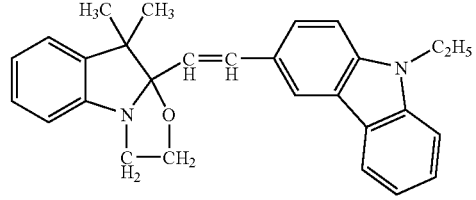

Dye 6
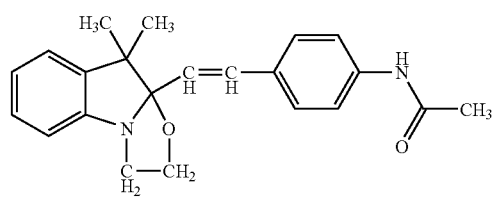

These compositions were applied to locks of natural and permanent-waved grey hair comprising 90% white hairs, at a rate of 5 g per 1 g of hair, at room temperature for 30 minutes. The locks were then rinsed with clear water.

After dyeing, the color of the locks was measured using a CM3600d spectrocolorimeter (specular components included, 10° angle, illuminant D65) in the CIE L*a*b* system. In this system, L* represents the intensity of the color, a* indicates the green/red color axis, and b* the blue/yellow color axis.

DEa*b* represents the variation in color between a lock of non-dyed hair and a lock of dyed hair, and is determined by means of the following formula:

$$\Delta E = \sqrt{(L^* - L_0^*)^2 + (a^* - a_0^*)^2 + (b^* - b_0^*)^2}$$

in which L*, a*, and b* represent the values measured on the dyed lock and $L_0^*$, $a_0^*$, and $b_0^*$ represent the values measured on the non-dyed lock.

The colorimetric results obtained are given in the table below.

|  | DEa*b* | Color |
| --- | --- | --- |
| Natural lock comprising 90% white hairs | | |
| Dye 1 | 57 | fuchsia |
| Dye 2 | 54 | blue |
| Dye 3 | 65 | violet |

| | DEa*b* | Color |
|---|---|---|
| Dye 4 | 41 | blue |
| Dye 5 | 42 | red |
| Dye 6 | 42 | yellow |
| Permanent-waved lock comprising 90% white hairs | | |
| Dye 1 | 57 | fuchsia |
| Dye 2 | 57 | blue |
| Dye 3 | 71 | violet |
| Dye 4 | 36 | blue |
| Dye 5 | 43 | red |
| Dye 6 | 47 | yellow |

A shampoo-fastness test was performed on the locks of hair dyed with dyes 1 and 2 obtained under the conditions described above. The dyed locks were subjected to 20 shampoo washes according to a cycle comprising wetting the locks with water, washing with shampoo, rinsing with water, and then drying.

The degradation of the color after x shampoo washes was estimated according to the following formula:

$$\% \text{ degradation} = 100 * \frac{DE\, xShamp}{DE\, Dyed}$$

wherein:

$$DE\, Dyed = \sqrt{(a^*\text{dyed} - a^*\text{ctrl})^2 + (b^*\text{dyed} - b^*\text{ctrl})^2 + (L^*\text{dyed} - L^*\text{ctrl})^2}$$

and $$DE\, xShamp = \sqrt{(a^*\text{dyed} - a^*\text{xSh})^2 + (b^*\text{dyed} - b^*\text{xSh})^2 + (L^*\text{dyed} - L^*\text{xSh})^2}$$

wherein $a^*_{ctrl}$, $b^*_{ctrl}$, and $L^*_{ctrl}$ are the values of a*, b*, and L* of the non-dyed lock; $a^*_{dyed}$, $b^*_{dyed}$, and $L^*_{dyed}$ are the values of a*, b*, and L* of the dyed lock before shampooing, whereas $a^*_{xSh}$, $b^*_{xSh}$, and $L^*_{xSh}$ are the values of a*, b*, and L* of the dyed lock after x shampoo washes.

| | L* | a* | b* | % degradation |
|---|---|---|---|---|
| Permanent-waved lock comprising 90% white hairs | | | | |
| Dye 1 | 23.5 | 34.6 | −5.0 | — |
| Dye 1 after 5 shampoo washes | 24.8 | 40.1 | −5.5 | 10 |
| Dye 1 after 12 shampoo washes | 28.3 | 42.8 | −4.5 | 17 |
| Dye 1 after 18 shampoo washes | 26.6 | 44.0 | −2.6 | 18 |
| Dye 1 after 20 shampoo washes | 28.7 | 47.4 | −4.3 | 24 |
| Natural lock comprising 90% white hairs | | | | |
| Dye 2 | 18.1 | 11.2 | −23.2 | — |
| Dye 2 after 5 shampoo washes | 18.4 | 9.2 | −23.6 | 4 |
| Dye 2 after 12 shampoo washes | 23.4 | 8.6 | −28.5 | 14 |
| Dye 2 after 18 shampoo washes | 24.4 | 6.3 | −29.6 | 18 |
| Dye 2 after 20 shampoo washes | 25.8 | 6.2 | −30.5 | 20 |
| Permanent-waved lock containing 90% white hairs | | | | |
| Dye 2 | 20.0 | 8.8 | −27.3 | — |
| Dye 2 after 5 shampoo washes | 19.3 | 7.9 | −24.0 | 6 |
| Dye 2 after 12 shampoo washes | 19.8 | 7.8 | −24.1 | 6 |
| Dye 2 after 18 shampoo washes | 20.6 | 7.4 | −23.7 | 7 |
| Dye 2 after 20 shampoo washes | 24.8 | 4.2 | −27.0 | 11 |

These results show that after 20 shampoo washes, the dyes that are useful in the context of the present disclosure show good fastness.

Example 7

The following dye composition was prepared:

| Constituent | Composition 7 |
|---|---|
| Dye* | 3 × 10⁻³ mol % |
| Ethanol | 15 g |
| Benzyl alcohol | 5 g |
| Benzoic acid | 0.2 g |
| Distilled water | qs 100 g |

*The dye used was:

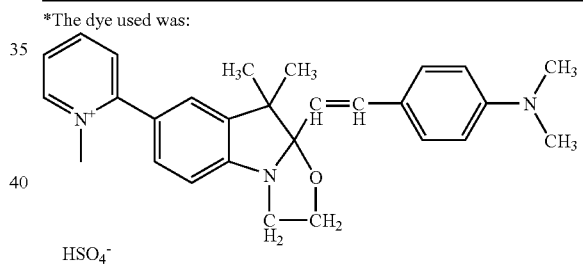

This composition was applied to locks of natural and permanent-waved grey hair comprising 90% white hairs, at a rate of 5 g per 1 g of hair, at room temperature for 30 minutes. The locks were then rinsed with clear water.

After dyeing, the color of the locks was chromatic violet.

What is claimed is:

1. A method for dyeing keratin fibers comprising applying to the keratin fibers a dye composition comprising, in a suitable dyeing medium, at least one compound chosen from compounds of formulas (I) and (II), and addition salts thereof:

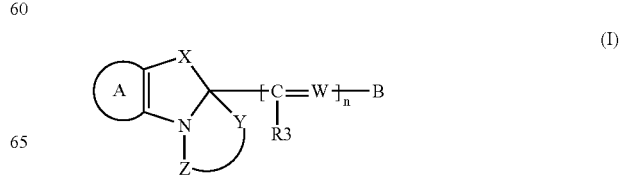

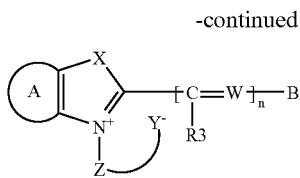

$$\text{(II)}$$

wherein:
A is chosen from substituted or unsubstituted, 5- to 16-membered, fused or non-fused, aromatic or heteroaromatic nuclei;

X is chosen from oxygen, sulfur, and $CR_1R_2$ groups;

$R_1$ and $R_2$, which may be identical or different, are chosen from hydrogen, $C_1$-$C_6$ alkyl radicals, $C_1$-$C_6$ hydroxyalkyl radicals, $C_1$-$C_6$ alkoxyalkyl radicals, and alkylene chains optionally comprising at least one atom chosen from oxygen and sulfur atoms; $R_1$ and $R_2$ may together form an aromatic or non-aromatic 5- or 6-membered ring optionally comprising at least one heteroatom chosen from nitrogen, oxygen, and sulfur;

$R_3$ is chosen from hydrogen, halogen atoms, $C_1$-$C_6$ alkyl radicals, cyano radicals, aromatic groups, phenoxy groups, and nitro radicals;

W is chosen from $CR_4$ groups and nitrogen;

$R_4$ is chosen from hydrogen, halogen atoms, $C_1$-$C_6$ alkyl radicals, cyano radicals, aromatic groups, phenoxy radicals, and nitro radicals.

Y is chosen from oxygen, sulfur, and $NR_5$ groups;

$R_5$ is chosen from hydrogen and $C_1$-$C_6$ alkyl radicals;

Z is chosen from —$C_pH_{2p}$— groups, wherein p is an integer ranging from 2 to 4, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals; —$C_qH_{2q}CO$— groups, wherein q is an integer ranging from 1 to 3, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals;

n is an integer from 1 to 4; and

B is chosen from substituted or unsubstituted, 5- to 16-membered, fused or non-fused aromatic or heteroaromatic nuclei.

2. The method of claim 1, wherein A is chosen from benzene, anthracene, naphthalene, and quinoline nuclei.

3. The method of claim 1, wherein A is optionally substituted with at least one group chosen from halo radicals, $C_1$-$C_6$ alkyl radicals, $C_1$-$C_6$ alkoxy radicals, $C_1$-$C_6$ alkylsulfonyl radicals (—$SO_2$-alkyl), $C_1$-$C_6$ alkylsulfonate radicals (—$SO_3$-alkyl), cyano radicals, trifluoromethyl radicals, $C_1$-$C_6$ alkylcarbonyl radicals, trifluoromethylsulfonyl radicals (—$SO_2$—$CF_3$), trifluoromethylcarbonyl radicals, phenylsulfonyl radicals (—$SO_2$-Ph), phenylsulfonate radicals (—$SO_3$-Ph), phenylcarbonyl radicals, nitro radicals, $C_1$-$C_6$ alkoxycarbonyl radicals, phosphonyl radicals (—$PO(OH)_2$), phosphonyl($C_1$-$C_6$)alkyl radicals (-alkyl-$PO(OH)_2$), hydroxyl radicals, amino radicals, di($C_1$-$C_6$)alkylamino radicals, (hydroxy($C_1$-$C_6$)alkyl)amino radicals, di(hydroxy($C_1$-$C_6$)alkyl)amino radicals, (amino($C_1$-$C_6$)-alkyl)amino radicals, di(amino($C_1$-$C_6$)alkyl)amino radicals, (hydroxy($C_1$-$C_6$)alkyl)((C_1$-$C_6$)-alkyl)amino radicals, (amino($C_1$-$C_6$)alkyl)((C_1$-$C_6$)alkyl)amino radicals, (amino($C_1$-$C_6$)alkyl)(hydroxy($C_1$-$C_6$)alkyl)amino radicals, hydroxy($C_1$-$C_6$)alkyl radicals, amino($C_1$-$C_6$)alkyl radicals, (($C_1$-$C_6$)alkyl)amino($C_1$-$C_6$)alkyl radicals, di(($C_1$-$C_6$)alkyl)amino($C_1$-$C_6$)alkyl radicals, (hydroxy($C_1$-$C_6$)alkyl)amino($C_1$-$C_6$)alkyl radicals, di(hydroxy($C_1$-$C_6$)alkyl)-amino($C_1$-$C_6$)alkyl radicals, (amino($C_1$-$C_6$)alkyl)amino($C_1$-$C_6$)alkyl radicals, di(amino($C_1$-$C_6$)alkyl)amino($C_1$-$C_6$)alkyl radicals, (($C_1$-$C_6$)alkyl)(hydroxy($C_1$-$C_6$)alkyl)amino($C_1$-$C_6$)alkyl radicals, (amino($C_1$-$C_6$)alkyl)(($C_1$-$C_6$)alkyl)amino radicals, (hydroxy($C_1$-$C_6$)alkyl)(($C_1$-$C_6$)alkyl)amino($C_1$-$C_6$)alkyl radicals; phenyl($C_1$-$C_6$)alkyl radicals optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals, cationic quaternary ammonium groups, $C_1$-$C_6$ alkyl radicals substituted with a cationic quaternary ammonium group, carboxyl radicals, ($C_1$-$C_6$)alkyl radicals substituted with a carboxyl radical, thio radicals, thio($C_1$-$C_6$)alkyl radicals, sulfonate radicals (—$SO_3^-$), ($C_1$-$C_6$)alkyl radicals substituted with a sulfonate radical, ($C_1$-$C_6$)alkylcarbonyl($C_1$-$C_6$)alkyl radicals, di(halo($C_1$-$C_6$)alkyl)amino radicals, acetamido radicals, aryloxy radicals, aryloxy-($C_1$-$C_6$)alkyl radicals, ethenyl radicals (—$CH=CH_2$), ethenylcarbonyl radicals (—$CO$—$CH=CH_2$); wherein two adjacent groups may possibly form an aromatic or heteroaromatic ring, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals, or a —O—$C_mH_{2m}$—O— ring wherein m is an integer equal to 1 or 2.

4. The method of claim 3, wherein A is optionally substituted with at least one group chosen from ($C_1$-$C_6$)alkylsulfonyl radicals; pyridinium and imidazolium groups which may be optionally substituted with at least one substituent chosen from halo, hydroxyl, alkyl, haloalkyl, alkoxy, amino, monoalkylamino, dialkylamino, monodihydroxyalkylamino, dihydroxyalkylamino, and carboxyl radicals; tri($C_1$-$C_6$)alkylammonium groups; and sulfonate radicals.

5. The method of claim 1, wherein X is chosen from $CR_1R_2$ groups.

6. The method of claim 1, wherein $R_1$ and $R_2$, which may be identical or different, are chosen from $C_1$-$C_6$ alkyl radicals.

7. The method of claim 1, wherein $R_3$ is hydrogen.

8. The method of claim 1, wherein W is chosen from $CR_4$ groups.

9. The method of claim 1, wherein $R_4$ is hydrogen.

10. The method of claim 1, wherein Y is oxygen.

11. The method of claim 1, wherein Z is chosen from —$C_pH_{2p}$— groups, wherein p is an integer ranging from 2 to 4, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals.

12. The method of claim 1, wherein n is equal to 1 or 2.

13. The method of claim 1, wherein B is chosen from benzene, carbazole, and indole nuclei.

14. The method of claim 1, wherein B is optionally substituted with at least one group chosen from halo radicals, $C_1$-$C_6$ alkyl radicals, $C_1$-$C_6$ alkoxy radicals, cyano radicals, trifluoromethyl radicals, $C_1$-$C_6$ alkylcarbonyl radicals, trifluoromethylsulfonyl radicals, trifluoromethylcarbonyl radicals, phenylsulfonyl radicals, phenylcarbonyl radicals, phenyl radicals optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals, acylamino radicals, hydroxyl radicals, amino radicals, di(($C_1$-$C_6$)alkyl) amino radicals, hydroxy($C_1$-$C_6$)alkylamino radicals, di(hydroxy($C_1$-$C_6$)alkyl)amino radicals, (amino($C_1$-$C_6$)alkyl) amino radicals, di(amino($C_1$-$C_6$)alkyl)amino radicals, (($C_1$-$C_6$)alkyl)(hydroxy($C_1$-$C_6$)alkyl)amino radicals, (amino($C_1$-$C_6$)alkyl)(($C_1$-$C_6$)alkyl)amino radicals, (amino($C_1$-$C_6$)alkyl) (hydroxy($C_1$-$C_6$)alkyl)amino radicals, hydroxy-($C_1$-$C_6$) alkyl radicals, amino($C_1$-$C_6$)alkyl radicals, ($C_1$-$C_6$) alkylamino($C_1$-$C_6$)alkyl radicals, di(($C_1$-$C_6$)alkyl)amino($C_1$-$C_6$)alkyl radicals, (hydroxy($C_1$-$C_6$)alkyl)amino($C_1$-$C_6$)alkyl radicals, di(hydroxy($C_1$-$C_6$)alkyl)amino($C_1$-$C_6$)alkyl radicals, amino($C_1$-$C_6$)alkylamino($C_1$-$C_6$)alkyl radicals, di(amino($C_1$-$C_6$)alkyl)amino($C_1$-$C_6$)alkyl radicals, (($C_1$-$C_6$) alkyl)(hydroxy($C_1$-$C_6$)-alkyl)amino($C_1$-$C_6$)alkyl radicals, (($C_1$-$C_6$)alkyl)(amino($C_1$-$C_6$)alkyl)amino radicals, (hydroxy ($C_1$-$C_6$)alkyl)(($C_1$-$C_6$)alkyl)amino($C_1$-$C_6$)alkyl radicals, phenyl($C_1$-$C_6$)alkyl radicals optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals, cationic quaternary ammonium groups, ($C_1$-$C_6$)alkyl radicals substituted with a cationic quaternary ammonium group, carboxyl radicals, ($C_1$-$C_6$)alkyl radicals substituted with a carboxyl radical, thio radicals, thio($C_1$-$C_6$) alkyl radicals, sulfonate radicals, ($C_1$-$C_6$)alkyl radicals substituted with a sulfonate radical, ($C_1$-$C_6$)alkylcarbonyl($C_1$-$C_6$)alkyl radicals, di(halo($C_1$-$C_6$)alkyl)amino radicals, acetamido radicals, aryloxy radicals, aryloxy($C_1$-$C_6$)alkyl radicals, ethenyl radicals, ethenylcarbonyl radicals, $NR_6R_7$ groups, wherein $R_6$ and $R_7$ may form, together with the nitrogen atom to which they are attached, a non-aromatic $C_5$, $C_6$, or $C_7$ ring, optionally interrupted with at least one heteroatom chosen from nitrogen, oxygen, and sulfur, alkylene chains optionally comprising at least one atom chosen from oxygen and sulfur and optionally ending with a group chosen from cyano, $C_1$-$C_6$ alkylsulfonyl, and $C_1$-$C_6$ alkylcarbonyl groups; wherein two adjacent groups of B may form an aromatic or heteroaromatic ring, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals, or a —O—$C_rH_{2r}$—O— ring, wherein r is an integer equal to 1 or 2.

15. The method of claim 14, wherein B is optionally substituted with at least one group chosen from hydroxyl radicals; amino radicals; di(($C_1$-$C_6$)alkyl)amino radicals; $C_1$-$C_6$ alkyl radicals; acetamido radicals; pyridinium groups; and tri($C_1$-$C_6$)alkylammonium groups.

16. The method of claim 1, wherein the compounds of formula (I) are chosen from 9a-[2-[4-(dimethylamino)phenyl]-1,3-butadienyl]-2,3,9, 9a-tetrahydro-9,9-dimethyloxazolo-[3,2-a]indole-7-carboxylic acid;

[9a-[2-[4-(dimethylamino)phenyl]ethenyl]-2,3,9,9a-tetrahydro-9,9-dimethyloxazolo-[3,2-a]indol-7-yl]phosphonic acid;

4-[2-(9,9-diethyl-2,3-dihydro-7-methoxyoxazolo[3,2-a] indol-9a(9H)-yl)ethenyl]-N,N-diethylbenzenamine;

[3-[9a-[2-[4-(dimethylamino)phenyl]ethenyl]-2,3,9,9a-tetrahydro-9,9-dimethyloxazolo[3,2-a]indol-7-yl]propyl]phosphonic acid;

4-[2-(2,3-dihydro-9,9-dimethyloxazolo[3,2-a]indol-9a (9H)-yl)ethenyl]-N-methyl-N-phenylbenzenamine;

4-[2-(2,3-dihydro-9,9-dimethyloxazolo[3,2-a]indol-9a (9H)-yl)ethenyl]-3-ethoxy-N,N-diethylbenzenamine;

4-[2-(2,3-dihydro-9,9-dimethyloxazolo[3,2-a]indol-9a (9H)-yl)ethenyl]-N-ethyl-N-(2-methylpropyl)benzenamine;

4-[2-(2,3-dihydrooxazolo[3,2-a]indol-9a(9H)-yl)ethenyl]-N,N-dimethylbenzenamine;

4-[4-(2,3-dihydro-7,9,9-trimethyloxazolo[3,2-a]indol-9a (9H)-yl)-1,3-butadienyl]-N,N-dimethylbenzenamine;

4-[4-(2,3-dihydro-9,9-dimethyl-7-nitrooxazolo[3,2-a]indol-9a(9H)-yl)-1,3-butadienyl]-N,N-dimethylbenzenamine; 9a-[4-[4-(dimethylamino)phenyl]-1,3-butadienyl]-2,3,9,9a-tetrahydro-9,9-dimethyloxazolo[3,2-a] indole-7-carbonitrile;

9a-[2-[4-(dimethylamino)phenyl]ethenyl]-2,3,9,9a-tetrahydro-9,9-dimethyloxazolo[3,2-a]indole-7-carbonitrile; 4-[2-(2,3-dihydro-9,9-dimethyloxazolo[3,2-a]indol-9a(9H)-yl)ethenyl]-N,N-dimethylbenzenamine;

9a-[2-[4-(dimethylamino)phenyl]ethenyl]-2,3,9,9a-tetrahydro-9,9-dimethyloxazolo-[3,2-a]indole-7-sulfonic acid methyl ester;

N,N-bis(2-chloroethyl)-4-[2-(2,3-dihydro-9,9-dimethyloxazolo[3,2-a]indol-9a(9H)-yl)ethenyl]benzenamine;

9a-[2-[4-(dimethylamino)phenyl]ethenyl]-9,9a-dihydro-9,9-dimethyl-7-(octylsulfonyl)oxazolo[3,2-a]indol-2 (3H)-one;

9a-[2-[4-(dimethylamino)phenyl]ethenyl]-9,9a-dihydro-9,9-dimethyl-7-(phenylsulfonyl)-oxazolo[3,2-a]indol-2(3H)-one;

9a-[2-[4-(dimethylamino)phenyl]-1-methylethenyl]-9,9a-dihydro-9,9-dimethyl-7-(methylsulfonyl)oxazolo[3,2-a]indol-2(3H)-one; 9a-[2-[4-(dimethylamino)phenyl] ethenyl]-9,9a-dihydro-9,9-dimethyl-7-(methylsulfonyl)oxazolo[3,2-a]indol-2(3H)-one;

4-[2-[2,3-dihydro-9,9-dimethyl-7-(methylsulfonyl)oxazolo[3,2-a]indol-9a(9H)-yl]ethenyl]-N,N-dimethylbenzenamine;

4-[2-[9-(ethoxymethyl)-2,3-dihydro-9-methyl-7-(methylsulfonyl)oxazolo[3,2-a]indol-9a(9H)-yl]ethenyl]-N,N-dimethylbenzenamine;

4-[2-[2,3-dihydro-2,9,9-trimethyl-7-(methylsulfonyl)oxazolo[3,2-a]indol-9a(9H)-yl]ethenyl]-N,N-dimethylbenzenamine;

4-[2-[2,3-dihydro-9,9-dimethyl-7-(methylsulfonyl)oxazolo[3,2-a]indol-9a(9H)-yl]-1-propenyl]-N,N-dimethylbenzenamine;

N,N-dibutyl-4-[2-[2,3-dihydro-9,9-dimethyl-7-(methylsulfonyl)oxazolo[3,2-a]indol-9a(9H)-yl]ethenyl]benzenamine;

4-[2-[2,3-dihydro-9,9-dimethyl-7-(phenylsulfonyl)oxazolo[3,2-a]indol-9a(9H)-yl]ethenyl]-N,N-dimethyl;

4-[2-[2,3-dihydro-9,9-dimethyl-7-(octylsulfonyl)oxazolo [3,2-a]indol-9a(9H)-yl]ethenyl]-N,N-dimethylbenzenamine;

N-[4-[2-[7-(butylsulfonyl)-2,3-dihydro-9,9-dimethyloxazolo[3,2-a]indol-9a(9H)-yl]ethenyl]phenyl]acetamide;

4-[2-[7-(butylsulfonyl)-2,3-dihydro-9,9-d imethyloxazolo [3,2-a]indol-9a(9H)-yl]ethenyl]-N,N-dimethylbenzenamine;

4-[4-[2,3-dihydro-9,9-dimethyl-7-(methylsulfonyl)oxazolo[3,2-a]indol-9a(9H)-yl]-1,3-butadienyl]-N,N-dimethylbenzenamine;

9a-[2-[4-(dimethylamino)phenyl]ethenyl]-2,3,9,9a-tetrahydro-9-methyloxazolo[3,2-a]indole-9-ethanol; 4-[2-(9,9-diethyl-2,3-dihydrooxazolo[3,2-a]indol-9a(9H)-yl)ethenyl]-N,N-dimethylbenzenamine;

4-[2-[2,3-dihydro-9-methyl-9-(2-phenoxyethyl)oxazolo [3,2-a]indol-9a(9H)-yl]ethenyl]-N,N-dimethylbenzenamine;

4-[2-[9-(ethoxymethyl)-2,3-dihydro-9-methyloxazolo[3, 2-a]indol-9a(9H)-yl]ethenyl]-N,N-dimethylbenzenamine;

4-[2-(11,11-dimethylbenz[e]oxazolo[3,2-a]indol-10a (1H)-yl)ethenyl]-N,N-dimethylbenzenamine;

4-[2-(7-methoxy-9,9-dimethyloxazolo[3,2-a]indol-9a (9H)-yl)ethenyl]-N,N-dimethylbenzenamine;

4-[2-(9,9-dimethyloxazolo[3,2-a]indol-9a(9H)-yl)ethenyl]-N, N-dimethylbenzenamine;

9a-[2-[4-(dimethylamino)phenyl]ethenyl]-3-ethyl-9,9a-dihydro-9,9-dimethyloxazolo[3,2-a]indol-2(3H)-one;

7-chloro-9a-[2-[4-(dimethylamino)phenyl]ethenyl]-9,9a-dihydro-3,9,9-trimethyloxazolo[3,2-a]indol-2(3H)-one;

9a-[2-[4-(dibutylamino)phenyl]ethenyl]-9,9a-dihydro-9, 9-dimethyloxazolo[3,2-a]indol-2(3H)-one;

9a-[2-[4-(dimethylamino)phenyl]ethenyl]-9,9a-dihydro-9-(2-hydroxyethyl)-9-methyloxazolo[3,2-a]indol-2 (3H)-one;

9a-[2-[4-(dimethylamino)phenyl]-1-propenyl]-9,9a-dihydro-9,9-dimethyloxazolo[3,2-a]indol-2(3H)-one;

9,9a-dihydro-7,9,9-trimethyl-9a-[2-(4-nitrophenyl)ethenyl]oxazolo[3,2-a]indol-2(3H)-one; N-[4-[2-(2,3-dihydro-9,9-dimethyl-2-oxooxazolo[3,2-a]indol-9a(9H)-yl) ethenyl]phenyl]acetamide;

9a-[2-[4-(dimethylamino)phenyl]ethenyl]-9,9a-dihydro-6-methoxy-9,9-dimethyloxazolo[3,2-a]indol-2(3H)-one;

9a-[2-[4-(dimethylamino)phenyl]ethenyl]-2,3,9,9a-tetrahydro-9,9-dimethyl-2-oxooxazolo[3,2-a]indole-7-carboxylic acid ethyl ester;

9a-[2-[4-(dimethylamino)phenyl]ethenyl]-9,9a-dihydro-7,9,9-trimethyloxazolo[3,2-a]indol-2(3H)-one;

10a-[2-[4-(dimethylamino)phenyl]ethenyl]-10a,11-dihydro-11,11-dimethylbenz[e]oxazolo[3,2-a]indol-9(8H)-one;

9,9a-dihydro-9,9-dimethyl-9a-[2-(4-nitrophenyl)ethenyl] oxazolo[3,2-a]indol-2(3H)-one; 7-chloro-9a-[2-[4-(dimethylamino)phenyl]ethenyl]-9,9a-dihydro-9,9-dimethyloxazolo[3,2-a]indol-2(3H)-one;

9a-[2-[4-(dimethylamino)phenyl]ethenyl]-9,9a-dihydro-9,9-dimethyloxazolo[3,2-a]indol-2(3H)-one;

4-[2-(7-chloro-2,3-dihydro-9,9-dimethyloxazolo[3,2-a] indol-9a(9H)-yl)ethenyl]-N,N-dimethylbenzenamine;

4-[2-(2,3-dihydro-9,9-dimethyloxazolo[3,2-a]indol-9a (9H)-yl)ethenyl]-N,N-dimethylbenzenamine;

4-[2-(7-chloro-2,3-dihydro-2,9,9-trimethyloxazolo[3,2-a] indol-9a(9H)-yl)ethenyl]-N,N-dimethylbenzenamine;

4-[2-(2,3-dihydro-9,9-dimethyloxazolo[3,2-a]indol-9a (9H)-yl)-1-methylethenyl]-N,N-dimethylbenzenamine;

4-[2-(2,3-dihydro-9,9-dimethyloxazolo[3,2-a]indol-9a (9H)-yl)ethenyl]-N,N-diethyl-benzenamine;

2,3,9,9a-tetrahydro-7-methoxy-9,9-dimethyl-9a-[2-(4-nitrophenyl)ethenyl]oxazolo[3,2-a]-indole;

4-[2-(2,3-dihydro-9,9-dimethyl-7-nitrooxazolo[3,2-a]indol-9a(9H)-yl)ethenyl]-N,N-dimethylbenzenamine;

N,N-dibutyl-4-[2-(2,3-dihydro-9,9-dimethyloxazolo[3,2-a]indol-9a(9H)-yl)ethenyl]benzenamine;

2,3,9,9a-tetrahydro-9,9-dimethyl-7-nitro-9a-[2-(4-nitrophenyl)ethenyl]oxazolo[3,2-a]indole;

7-chloro-2,3,9,9a-tetrahydro-9,9-dimethyl-9a-[2-(4-nitrophenyl)ethenyl]oxazolo[3,2-a]indole;

4-[2-(2,3-dihydro-7-iodo-9,9-dimethyloxazolo[3,2-a]indol-9a(9H)-yl)ethenyl]-N,N-dimethylbenzenamine;

4-[2-(2,3-dihydro-5-methoxy-9,9-dimethyloxazolo[3,2-a]indol-9a(9H)-yl)ethenyl]-N,N-dimethylbenzenamine;

4-[2-(2,3-dihydro-7-methoxy-9,9-dimethyloxazolo[3,2-a]indol-9a(9H)-yl)ethenyl]-N,N-dimethylbenzenamine;

4-[4-(2,3-dihydro-9,9-dimethyloxazolo[3,2-a]indol-9a (9H)-yl)-1,3-butadienyl]-N,N-diethylbenzenamine;

4-[4-(7-chloro-2,3-dihydro-9,9-dimethyloxazolo[3,2-a] indol-9a(9H)-yl)-1,3-butadienyl]-N,N-dimethylbenzenamine;

4-[4-(2,3-dihydro-9,9-dimethyloxazolo[3,2-a]indol-9a (9H)-yl)-1,3-butadienyl]-N,N-dimethylbenzenamine;

4-[4-(2,3-dihydro-7-methoxy-9,9-dimethyloxazolo[3,2-a]indol-9a(9H)-yl)-1,3-butadienyl]-N,N-dimethylbenzenamine;

2,3,9,9a-tetrahydro-7,9,9-trimethyl-9a-[2-(4-nitrophenyl) ethenyl]oxazolo[3,2-a]indole; N-[4-[2-(2,3-dihydro-9, 9-dimethyloxazolo[3,2-a]indol-9a(9H)-yl)ethenyl]phenyl]acetamide;

4-[2-(2,3-dihydro-6-methoxy-9,9-dimethyloxazolo[3,2-a]indol-9a(9H)-yl)ethenyl]-N,N-dimethylbenzenamine;

4-[2-(8,9-dihydro-11,11-dimethylbenz[e]oxazolo[3,2-a] indol-10a(11H)-yl)ethenyl]-N,N-dimethylbenzenamine;

4-[2-(2,3-dihydro-7,9,9-trimethyloxazolo[3,2-a]indol-9a (9H)-yl)ethenyl]-N,N-dimethylbenzenamine;

2,3,9,9a-tetrahydro-9,9-dimethyl-9a-[2-(4-nitrophenyl) ethenyl]oxazolo[3,2-a]indole;

9,9a-dihydro-9,9-dimethyl-9a-[2-(9-methyl-9H-carbazol-3-yl)ethenyl]-7-(methylsulfonyl)-oxazolo[3,2-a]indol-2(3H)-one;

9a-[2-(9-hexyl-9H-carbazol-3-yl)ethenyl]-2,3,9,9a-tetrahydro-9,9-dimethyl-7-(phenylsulfonyl)oxazolo[3,2-a]indole;

2,3,9,9a-tetrahydro-9,9-dimethyl-7-(methylsulfonyl)-9a-[2-(9-octyl-9H-carbazol-3-yl)ethenyl]oxazolo[3,2-a] indole;

9a-[2-(9-butyl-6-methoxy-9H-carbazol-3-yl)ethenyl]-2,3, 9,9a-tetrahydro-9,9-dimethyloxazolo[3,2-a]indole-7-carboxylic acid ethyl ester;

9a-[2-(9-ethyl-9H-carbazol-3-yl)ethenyl]-2,3,9,9a-tetrahydro-9,9-dimethyloxazolo[3,2-a]indole-7-sulfonic acid methyl ester;

3-chloro-6-[2-[2,3-dihydro-9,9-dimethyl-7-(methylsulfonyl)oxazolo[3,2-a]indol-9a(9H)-yl]ethenyl]-9-octyl-9H-carbazole;

3-[2-[2,3-dihydro-9,9-dimethyl-7-(methylsulfonyl)oxazolo[3,2-a]indol-9a(9H)-yl]ethenyl]-9-methyl-9H-carbazole;

3-[2-9-(2-ethoxyethyl)-2,3-dihydro-9-methyl-7-(methylsulfonyl)oxazolo[3,2-a]indol-9a(9H)-yl]ethenyl]-9H-carbazole;

9a-[2-(9-hexyl-9H-carbazol-3-yl)ethenyl]-2,3,9,9a-tetrahydro-9-(2-hydroxyethyl)-9-methyloxazolo[3,2-a]indole-7-carboxylic acid ethyl ester;

2,3,9,9a-tetrahydro-9,9-dimethyl-9a-[2-(9-octyl-9H-carbazol-3-yl)ethenyl]oxazolo[3,2-a]indole-7-carboxylic acid ethyl ester;

9a-[2-(9-butyl-9H-carbazol-3-yl)ethenyl]-2,3,9,9a-tetrahydro-9,9-dimethyloxazolo[3,2-a]indole-7-carboxylic acid ethyl ester;

2,3,9,9a-tetrahydro-9,9-dimethyl-9a-[2-(9-methyl-9H-carbazol-3-yl)ethenyl]oxazolo[3,2-a]indole-7-carboxylic acid ethyl ester;

9a-[2-(9-butyl-6-ethoxy-9H-carbazol-3-yl)ethenyl]-2,3,9,9a-tetrahydro-N,N,9,9-tetramethyloxazolo[3,2-a]indol-7-amine;

2,3,9,9a-tetrahydro-9-methyl-9a-[2-(9-methyl-9H-carbazol-3-yl)ethenyl]oxazolo[3,2-a]indole-9-ethanol;

9a-[2-(9-butyl-9H-carbazol-3-yl)ethenyl]-2,3,9,9a-tetrahydro-N,N,9,9-tetramethyloxazolo[3,2-a]indol-7-amine;

3-[2-(2,3-dihydro-6-methoxy-9,9-dimethyloxazolo[3,2-a]indol-9a(9H)-yl)ethenyl]-9-methyl-9H-carbazole;

3-[2-(2,3-dihydro-9,9-dimethyloxazolo[3,2-a]indol-9a(9H)-yl)-1-propenyl]-9-methyl-9H-carbazole;

3-[2-(7-chloro-2,3-dihydro-9,9-dimethyloxazolo[3,2-a]indol-9a(9H)-yl)ethenyl]-9-methyl-9H-carbazole;

3-bromo-6-[2-(2,3-dihydro-9,9-dimethyloxazolo[3,2-a]indol-9a(9H)-yl)ethenyl]-9-ethyl-9H-carbazole; and 3-[2-(2,3-dihydro-9,9-dimethyloxazolo[3,2-a]indol-9a(9H)-yl)ethenyl]-9-methyl-9H-carbazole.

17. The method of claim 16, wherein the compounds of formula (I) are chosen from:

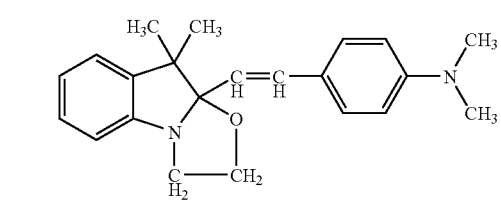

Dye 1

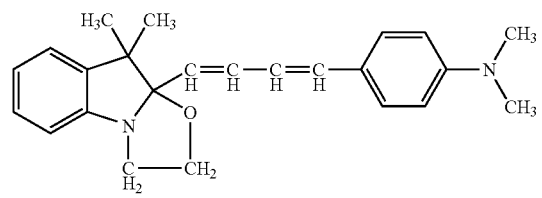

Dye 2

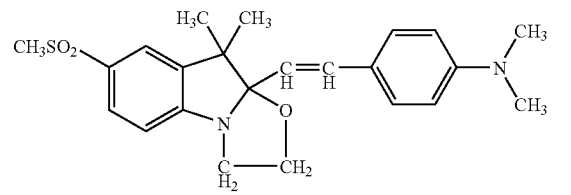

Dye 3

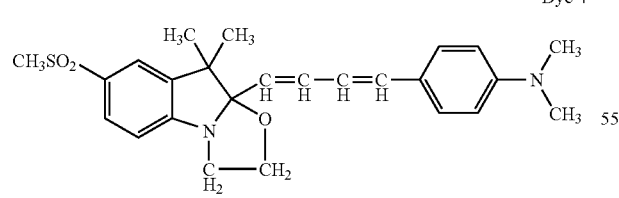

Dye 4

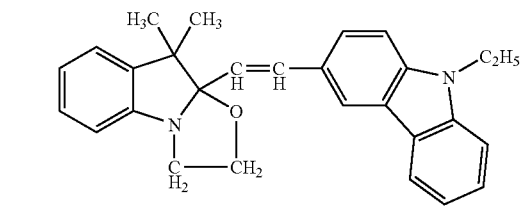

Dye 5

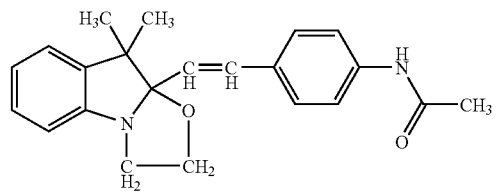

Dye 6

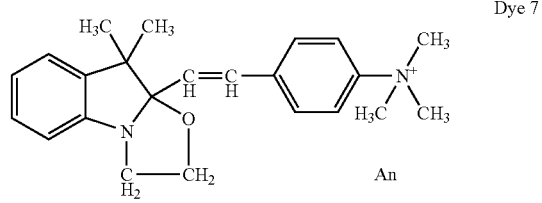

Dye 7

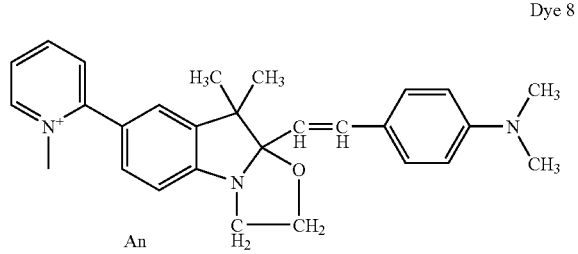

Dye 8

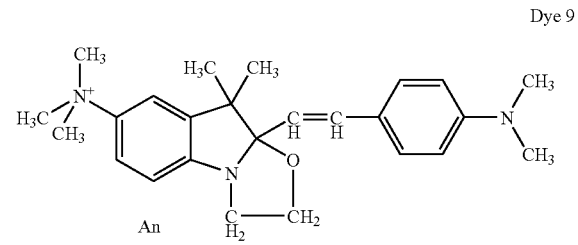

Dye 9

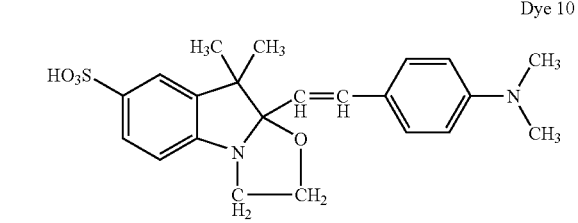

Dye 10

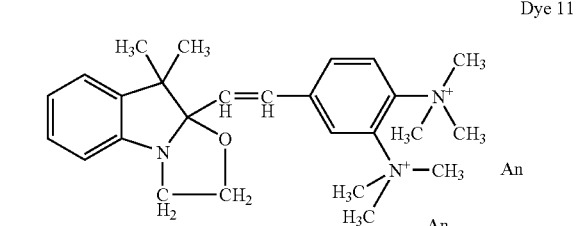

Dye 11 wherein An, which may be identical or different, is a negative counterion.

18. The method of claim 1, wherein the at least one compound chosen from compounds of formulas (I) and (II), and addition salts thereof, is present in the composition in an amount ranging from 0.0001% to 10% by weight relative to the total weight of the composition.

19. The method of claim 1, wherein the dye composition further comprises at least one agent chosen from acidifying agents and basifying agents.

20. The method of claim 19, wherein the acidifying agents are chosen from mineral acids and organic acids.

21. The method of claim 19, wherein the basifying agents are chosen from:

basic amino acids;

alkali metal and alkaline-earth metal carbonates and bicarbonates;

silicates and metasilicates;

compounds of formula (III):

$$X(OH)_n \qquad (III)$$

wherein:
when n is equal to 1, X is chosen from potassium, lithium, sodium, and ammonium ions $N^+R_8R_9R_{10}R_{11}$, wherein $R_8$, $R_9$, $R_{10}$, and $R_{11}$, which may be identical or different, are chosen from $C_2$-$C_4$ alkyl radicals; and when n is equal to 2, X is chosen from magnesium and calcium;

compounds of formula (IV):

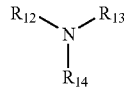

(IV)

wherein:

$R_{12}$ is chosen from hydrogen; $C_1$-$C_6$ alkyl radicals; $C_1$-$C_6$ monohydroxyalkyl radicals; and $C_2$-$C_6$ polyhydroxyalkyl radicals; and $R_{13}$ and $R_{14}$, which may be identical or different, are chosen from hydrogen; $C_1$-$C_6$ alkyl radicals; $C_1$-$C_6$ monohydroxyalkyl radicals; and $C_2$-$C_6$ polyhydroxyalkyl radicals; and compound of formula (V):

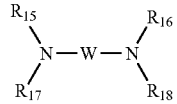

(V)

wherein:

W is a propylene residue optionally substituted with at least one entity chosen from hydroxyl group and $C_1$-$C_4$ alkyl radicals;

$R_{15}$, $R_{16}$, $R_{17}$, and $R_{18}$, which may be identical or different, are chosen from hydrogen, $C_1$-$C_4$ alkyl radicals, and $C_1$-$C_4$ hydroxyalkyl radicals.

22. The method of claim 1, wherein the suitable dyeing medium is chosen from water, organic solvents, and mixtures of water and at least one organic solvent.

23. The method of claim 22, wherein the at least one solvent is chosen from ketones; linear or branched monoalcohols and diols comprising from 2 to 10 carbon atoms; aromatic alcohols; polyols and polyol ethers; and diethylene glycol alkyl ethers.

24. The method of claim 22, wherein the suitable dyeing medium is chosen from water and mixtures of water and at least one organic solvent, and the pH ranges from 2 to 12.

25. The method of claim 1, wherein the dye composition further comprises at least one additive chosen from anionic, cationic, nonionic, amphoteric, and zwitterionic surfactants and mixtures thereof; anionic, cationic, nonionic, amphoteric, and zwitterionic polymers and mixtures thereof; mineral and organic thickeners; antioxidants; penetrants; sequestrants; fragrances; buffers; dispersants; conditioning agents; preserving agents; and opacifiers.

26. A process for treating keratin fibers, comprising applying a dye composition to the keratin fibers for a leave-on time sufficient to develop a desired coloration, optionally followed by rinsing, wherein the dye composition comprises, in a suitable dyeing medium, at least one compound chosen from compounds of formulas (I) and (II), and addition salts thereof:

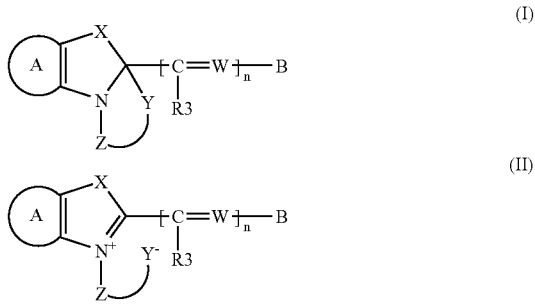

wherein:

A is chosen from substituted or unsubstituted, 5- to 16-membered, fused or non-fused aromatic or heteroaromatic nuclei;

X is chosen from oxygen, sulfur, and $CR_1R_2$ groups;

$R_1$ and $R_2$, which may be identical or different, are chosen from hydrogen, $C_1$-$C_6$ alkyl radicals, $C_1$-$C_6$ hydroxyalkyl radicals, $C_1$-$C_6$ alkoxyalkyl radicals, and alkylene chains optionally comprising at least one atom chosen from oxygen and sulfur atoms; and $R_1$ and $R_2$ may together form an aromatic or non-aromatic 5- or 6-membered ring optionally comprising at least one heteroatom chosen from nitrogen, oxygen, and sulfur;

$R_3$ is chosen from hydrogen, halogen atoms, $C_1$-$C_6$ alkyl radicals, cyano radicals, aromatic groups, phenoxy groups, and nitro radicals;

W is chosen from $CR_4$ groups and nitrogen;

$R_4$ is chosen from hydrogen, halogen atoms, $C_1$-$C_6$ alkyl radicals, cyano radicals, aromatic groups, phenoxy radicals, and nitro radicals.

Y is chosen from oxygen, sulfur, and $NR_5$ groups;

$R_5$ is chosen from hydrogen and $C_1$-$C_6$ alkyl radicals;

Z is chosen from —$C_pH_{2p}$— groups, wherein p is an integer ranging from 2 to 4, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals; —$C_qH_{2q}CO$— groups, wherein q is an integer ranging from 1 to 3, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals;

n is an integer from 1 to 4; and

B is chosen from substituted or unsubstituted, 5- to 16-membered, fused or non-fused aromatic or heteroaromatic nuclei.

27. The process of claim 26, further comprising a pre- or post-treatment of the keratin fibers allowing development of the coloration.

28. The process of claim 27, wherein the pre- or post-treatment comprises treating the fibers via the action of an external agent chosen from light, electrical current, heat, acidifying agents, basifying agents, solvents, and/or electromagnetic radiation.

29. The process of claim 26, wherein the dye composition is applied to the keratin fibers in the presence of at least one oxidizing agent.

30. The process of claim 29, wherein the at least one oxidizing agent is chosen from hydrogen peroxide, urea peroxide, alkali metal bromates, persalts, peracids, and oxidase enzymes.

31. A multi-compartment device comprising at least one first compartment containing at least one dye composition, and at least one second compartment comprising at least one agent chosen from acidifying agents, basifying agents, and/or solvents, wherein the at least one dye composition comprises, in a suitable dyeing medium, at least one compound chosen from compounds of formulas (I) and (II), and addition salts thereof:

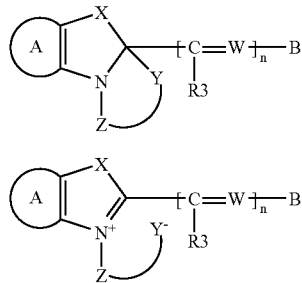

wherein:
A is chosen from substituted or unsubstituted, 5- to 16-membered, fused or non-fused aromatic or heteroaromatic nuclei;
X is chosen from oxygen, sulfur, and $CR_1R_2$ groups;
$R_1$ and $R_2$, which may be identical or different, are chosen from hydrogen, $C_1$-$C_6$ alkyl radicals, $C_1$-$C_6$ hydroxyalkyl radicals, $C_1$-$C_6$ alkoxyalkyl radicals, and alkylene chains optionally comprising at least one atom chosen from oxygen and sulfur atoms; and $R_1$ and $R_2$ may together form an aromatic or non-aromatic 5- or 6-membered ring optionally comprising at least one heteroatom chosen from nitrogen, oxygen, and sulfur;
$R_3$ is chosen from hydrogen, halogen atoms, $C_1$-$C_6$ alkyl radicals, cyano radicals, aromatic groups, phenoxy groups, and nitro radicals;
W is chosen from $CR_4$ groups and nitrogen;
$R_4$ is chosen from hydrogen, halogen atoms, $C_1$-$C_6$ alkyl radicals, cyano radicals, aromatic groups, phenoxy radicals, and nitro radicals
Y is chosen from oxygen, sulfur, and $NR_5$ groups;
$R_5$ is chosen from hydrogen and $C_1$-$C_6$ alkyl radicals;
Z is chosen from —$C_pH_{2p}$— groups, wherein p is an integer ranging from 2 to 4, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals; —$C_qH_{2q}CO$— groups, wherein q is an integer ranging from 1 to 3, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals;
n is an integer from 1 to 4; and
B is chosen from substituted or unsubstituted, 5- to 16-membered, fused or non-fused aromatic or heteroaromatic nuclei.

32. The device of claim 31, further comprising at least one third compartment containing at least one oxidizing agent.

33. A compound chosen from compounds of formulas (I) and (II), and addition salts thereof, wherein the compound comprises at least one cationic quaternary ammonium group:

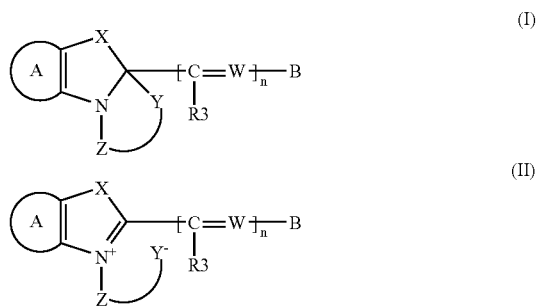

wherein:
A is chosen from substituted or unsubstituted, 5- to 16-membered, fused or non-fused aromatic or heteroaromatic nuclei;
X is chosen from oxygen, sulfur, and $CR_1R_2$ groups;
$R_1$ and $R_2$, which may be identical or different, are chosen from hydrogen, $C_1$-$C_6$ alkyl radicals, $C_1$-$C_6$ hydroxyalkyl radicals, $C_1$-$C_6$ alkoxyalkyl radicals, and alkylene chains optionally comprising at least one atom chosen from oxygen and sulfur atoms; and $R_1$ and $R_2$ may together form an aromatic or non-aromatic 5- or 6-membered ring optionally comprising at least one heteroatom chosen from nitrogen, oxygen, and sulfur;
$R_3$ is chosen from hydrogen, halogen atoms, $C_1$-$C_6$ alkyl radicals, cyano radicals, aromatic groups, phenoxy groups, and nitro radicals;
W is chosen from $CR_4$ groups and nitrogen;
$R_4$ is chosen from hydrogen, halogen atoms, $C_1$-$C_6$ alkyl radicals, cyano radicals, aromatic groups, phenoxy radicals, and nitro radicals
Y is chosen from oxygen, sulfur, and $NR_5$ groups;
$R_5$ is chosen from hydrogen and $C_1$-$C_6$ alkyl radicals;
Z is chosen from —$C_pH_{2p}$— groups, wherein p is an integer ranging from 2 to 4, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals; —$C_qH_{2q}CO$— groups, wherein q is an integer ranging from 1 to 3, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals;
n is an integer from 1 to 4; and
B is chosen from substituted or unsubstituted, 5- to 16-membered, fused or non-fused aromatic or heteroaromatic nuclei.

34. The compound of claim 33, wherein the at least one cationic quaternary ammonium group is chosen from tri($C_1$-

$C_6$)alkylammonium, oxazolium, thiazolium, imidazolium, pyrazolium, pyridinium, pyrrolium, triazolium, isoxazolium, isothiazolium, pyrimidinium, pyrazinium, triazinium, pyridazinium, indolium, quinolinium, and isoquinolinium groups, which may be substituted or unsubstituted.

35. A dye composition comprising, in a suitable dyeing medium, at least one compound chosen from compounds of formulas (I) and (II), and addition salts thereof, wherein the at least one compound comprises at least one cationic quaternary ammonium group:

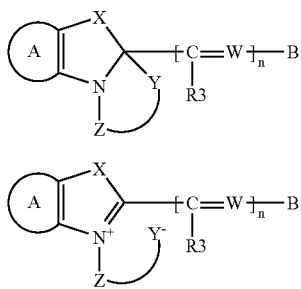

wherein:
A is chosen from substituted or unsubstituted, 5- to 16-membered, fused or non-fused aromatic or heteroaromatic nuclei;
X is chosen from oxygen, sulfur, and $CR_1R_2$ groups;
$R_1$ and $R_2$, which may be identical or different, are chosen from hydrogen, $C_1$-$C_6$ alkyl radicals, $C_1$-$C_6$ hydroxyalkyl radicals, $C_1$-$C_6$ alkoxyalkyl radicals, and alkylene chains optionally comprising at least one atom chosen from oxygen and sulfur atoms; and $R_1$ and $R_2$ may together form an aromatic or non-aromatic 5- or 6-membered ring optionally comprising at least one heteroatom chosen from nitrogen, oxygen, and sulfur;
$R_3$ is chosen from hydrogen, halogen atoms, $C_1$-$C_6$ alkyl radicals, cyano radicals, aromatic groups, phenoxy groups, and nitro radicals;
W is chosen from $CR_4$ groups and nitrogen;
$R_4$ is chosen from hydrogen, halogen atoms, $C_1$-$C_6$ alkyl radicals, cyano radicals, aromatic groups, phenoxy radicals, and nitro radicals;
Y is chosen from oxygen, sulfur, and $NR_5$ groups;
$R_5$ is chosen from hydrogen and $C_1$-$C_6$ alkyl radicals;
Z is chosen from —$C_pH_{2p}$— groups, wherein p is an integer ranging from 2 to 4, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals; —$C_qH_{2q}CO$— groups, wherein q is an integer ranging from 1 to 3, which may be optionally substituted with at least one substituent chosen from halo, hydroxyl, alkyl, haloalkyl, alkoxy, amino, monoalkylamino, dialkylamino, monohydroxyalkylamino, dihydroxyalkylamino, and carboxyl radicals;
n is an integer from 1 to 4; and
B is chosen from substituted or unsubstituted, 5- to 16-membered, fused or non-fused aromatic or heteroaromatic nuclei.

* * * * *

UNITED STATES PATENT AND TRADEMARK OFFICE
CERTIFICATE OF CORRECTION

| | | |
|---|---|---|
| PATENT NO. | : 7,399,319 B2 | Page 1 of 2 |
| APPLICATION NO. | : 11/491109 | |
| DATED | : July 15, 2008 | |
| INVENTOR(S) | : Grégory Plos | |

It is certified that error appears in the above-identified patent and that said Letters Patent is hereby corrected as shown below:

In claim 1, column 27, line 29, "radicals." should read --radicals;--.

In claim 3, column 28, lines 7-8, "(($C_1$-$C_6$)al kyl)(hydroxy($C_1$-$C_6$) alkyl)amino($C_1$-$C_6$)alkyl" should read --(($C_1$-$C_6$)alkyl)(hydroxy($C_1$-$C_6$)alkyl)amino($C_1$-$C_6$)alkyl--.

In claim 16, column 30, lines 58-60, "4-[2-[7-(butylsulfonyl)-2,3-dihydro-9,9-d imethyloxazolo [3,2-a]indol-9a(9H)-yl]ethenyl-N,N-dimethylbenzenamine;" should read --4-[2-[7-(butylsulfonyl)-2,3-dihydro-9,9-dimethyloxazolo[3,2-a]indol-9a(9H)-yl]ethenyl-N,N-dimethylbenzenamine;--.

In claim 16, column 31, lines 7-8, "4-[2-(11,11-dimethylbenz[e]oxazolo[3,2-a]indol-10a (1H)-yl)ethenyl]-N,N-dimethylbenzenamine;" should read --4-[2-(11,11-dimethylbenz[e]oxazolo[3,2-a]indol-10a(11H)-yl)ethenyl]-N,N-dimethylbenzenamine;--.

In claim 16, column 33, lines 12-13, "3-[2-(2,3-dihydro-9 ,9-dimethyloxazolo [3,2-a]indol-9a (9H)-yl)-1-propenyl]-9-methyl-9H-carbazole;" should read --3-[2-(2,3-dihydro-9,9-dimethyloxazolo[3,2-a]indol-9a(9H)-yl)-1-propenyl]-9-methyl-9H-carbazole;--.

In claim 21, column 35, line 37, "compound" should read --compounds--.

In claim 21, column 35, line 47, "a propylene residue" should read --chosen from propylene residues--.

In claim 21, column 35, line 48, "at least one" should read --an--.

In claim 21, column 35, line 48, "group" should read --groups--.

In claim 21, column 35, line 49, "radicals;" should read --radicals; and--.

In claim 26, column 36, line 45, "radicals." should read --radicals;--.

UNITED STATES PATENT AND TRADEMARK OFFICE
CERTIFICATE OF CORRECTION

PATENT NO.       : 7,399,319 B2
APPLICATION NO.  : 11/491109
DATED            : July 15, 2008
INVENTOR(S)      : Grégory Plos It is certified that error appears in the above-identified patent and that said Letters Patent is hereby corrected as shown below:

In claim 31, column 37, line 16, "agents,and/or" should read --agents, and/or--.

Signed and Sealed this

Ninth Day of September, 2008

JON W. DUDAS
*Director of the United States Patent and Trademark Office*